United States Patent
Chandratillake et al.

(10) Patent No.: US 11,640,405 B2
(45) Date of Patent: *May 2, 2023

(54) METHODS FOR ANALYZING GENOTYPES

(71) Applicant: Personalis, Inc., Menlo Park, CA (US)

(72) Inventors: Gemma L. Chandratillake, Cambridge (GB); Sarah K. Garcia, Palo Alto, CA (US); Richard Chen, Burlingame, CA (US); Michael James Clark, Foster City, CA (US)

(73) Assignee: Personalis, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/108,372

(22) Filed: Dec. 1, 2020

(65) Prior Publication Data

US 2021/0294810 A1 Sep. 23, 2021

Related U.S. Application Data

(63) Continuation of application No. 15/929,318, filed on Apr. 24, 2017, now abandoned, which is a
(Continued)

(51) Int. Cl.
*G06F 16/2457* (2019.01)
*G16B 50/00* (2019.01)
(Continued)

(52) U.S. Cl.
CPC ...... *G06F 16/24578* (2019.01); *G06F 16/248* (2019.01); *G16B 20/00* (2019.02);
(Continued)

(58) Field of Classification Search
CPC . G06F 16/24578; G06F 16/248; G16B 20/20; G16B 20/00; G16B 50/10; G16B 50/00
See application file for complete search history.

(56) References Cited

U.S. PATENT DOCUMENTS

| | | | |
|---|---|---|---|
| 4,458,066 A | 7/1984 | Caruthers et al. | |
| 4,683,202 A | 7/1987 | Mullis | |

(Continued)

FOREIGN PATENT DOCUMENTS

| | | |
|---|---|---|
| EP | 0281927 A2 | 9/1988 |
| EP | 1342794 B1 | 9/2003 |

(Continued)

OTHER PUBLICATIONS

ARUP's product "Exome Sequencing Symptom-Guided Analysis". http://www.aruplab.com/guides/ug/tests/2006332.jsp. Accessed Oct. 1, 2014.
(Continued)

*Primary Examiner* — Huawen A Peng
(74) *Attorney, Agent, or Firm* — Orrick, Herrington & Sutcliffe, LLP

(57) ABSTRACT

The disclosure provides methods and systems for analyzing genotype data. In some embodiments, a computer-implemented method comprises receiving data relating to one or more phenotypes of a subject or family members thereof, and ranking genes based on their association score with one or more phenotypes. Next, an output of the data is generated, the output comprising a comparison of the data based on the association score. The comparison can be in at least one of numeric and graphic form.

16 Claims, 4 Drawing Sheets

| 205 | 210 | 215 |
|---|---|---|
| Determination of the most likely Mendelian pattern of inheritance based on the clinical attributes and reported family history. | Generation of expected genotypes for all sequenced members of the family for all inheritance patterns. Genotypes ranked by 1) Parsimony to represent a particular inheritance pattern 2) Likelihood that the inheritance pattern explains the segregation of phenotype in the family. | Annotation of observed genotypes detected in sequenced individual with inheritance rank. |

Related U.S. Application Data continuation of application No. 16/570,219, filed on Sep. 13, 2019, now abandoned, which is a continuation of application No. 16/255,762, filed on Jan. 23, 2019, now abandoned, which is a continuation of application No. 15/083,058, filed on Mar. 28, 2016, now Pat. No. 10,255,330, which is a continuation of application No. PCT/US2014/059103, filed on Oct. 3, 2014.

(60) Provisional application No. 61/886,555, filed on Oct. 3, 2013.

(51) Int. Cl.
*G16B 20/20* (2019.01)
*G06F 16/248* (2019.01)
*G16B 20/00* (2019.01)
*G16B 50/10* (2019.01)

(52) U.S. Cl.
CPC ............ *G16B 20/20* (2019.02); *G16B 50/00* (2019.02); *G16B 50/10* (2019.02)

(56) References Cited

U.S. PATENT DOCUMENTS

| | | |
|---|---|---|
| 4,988,617 A | 1/1991 | Landegren et al. |
| 5,143,854 A | 9/1992 | Pirrung et al. |
| 5,242,794 A | 9/1993 | Whiteley et al. |
| 5,299,491 A | 4/1994 | Kawada |
| 5,382,510 A | 1/1995 | Levine et al. |
| 5,412,087 A | 5/1995 | McGall et al. |
| 5,432,065 A | 7/1995 | Fuller |
| 5,472,672 A | 12/1995 | Brennan |
| 5,494,810 A | 2/1996 | Barany et al. |
| 5,641,658 A | 6/1997 | Adams et al. |
| 5,928,907 A | 7/1999 | Woudenberg et al. |
| 6,015,674 A | 1/2000 | Woudenberg et al. |
| 6,045,996 A | 4/2000 | Cronin et al. |
| 6,582,938 B1 | 6/2003 | Su et al. |
| 6,754,655 B1 | 6/2004 | Segal |
| 6,818,395 B1 | 11/2004 | Quake et al. |
| 7,169,560 B2 | 1/2007 | Lapidus et al. |
| 7,211,390 B2 | 5/2007 | Rothberg et al. |
| 7,211,654 B2 | 5/2007 | Gao et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,282,337 B1 | 10/2007 | Harris |
| 7,300,788 B2 | 11/2007 | Matsuzaki et al. |
| 7,323,305 B2 | 1/2008 | Leamon et al. |
| 7,335,762 B2 | 2/2008 | Rothberg et al. |
| 7,361,488 B2 | 4/2008 | Fan et al. |
| 7,534,561 B2 | 5/2009 | Sana et al. |
| 7,582,420 B2 | 9/2009 | Oliphant et al. |
| 7,785,783 B2 | 8/2010 | Morley et al. |
| 7,803,550 B2 | 9/2010 | Makarov et al. |
| 8,026,094 B2 | 9/2011 | Green et al. |
| 8,140,270 B2 | 3/2012 | Kingsmore et al. |
| 8,415,101 B2 | 4/2013 | Garner |
| 8,417,459 B2 | 4/2013 | Reese et al. |
| 8,532,930 B2 | 9/2013 | Rabinowitz et al. |
| 8,589,175 B2 | 11/2013 | Glauser et al. |
| 8,785,353 B2 | 7/2014 | Van Eijk et al. |
| 8,862,410 B2 | 10/2014 | Hatchwell et al. |
| 9,109,256 B2 | 8/2015 | Shuber |
| 9,128,861 B2 | 9/2015 | Bartha et al. |
| 9,141,913 B2* | 9/2015 | Kupershmidt ...... G06F 16/2246 |
| 9,183,496 B2 | 11/2015 | Harris et al. |
| 9,228,232 B2 | 1/2016 | Faham et al. |
| 9,416,422 B2 | 8/2016 | Cheung |
| 9,453,257 B2 | 9/2016 | Hoyal-Wrightson et al. |
| 9,512,485 B2 | 12/2016 | Richardson et al. |
| 9,727,692 B2 | 8/2017 | Harris et al. |
| 9,745,626 B2 | 8/2017 | Bartha et al. |
| 9,909,186 B2 | 3/2018 | Schultz |
| 10,032,000 B1 | 7/2018 | Harris et al. |
| 10,174,375 B2 | 1/2019 | Lo et al. |
| 10,255,330 B2 | 3/2019 | Gemma et al. |
| 10,262,103 B2 | 4/2019 | Lehrer et al. |
| 10,266,890 B2 | 4/2019 | Bartha et al. |
| 10,415,091 B2 | 9/2019 | Bartha et al. |
| 10,711,306 B2 | 7/2020 | Shiina et al. |
| 10,738,355 B2 | 8/2020 | Sahin et al. |
| 10,900,088 B2 | 1/2021 | Vogelstein et al. |
| 11,047,006 B2 | 6/2021 | Salk et al. |
| 11,155,867 B2 | 10/2021 | Bartha et al. |
| 11,286,530 B2 | 3/2022 | Rabinowitz et al. |
| 2002/0006615 A1 | 1/2002 | Goldsborough et al. |
| 2002/0164629 A1 | 11/2002 | Quake et al. |
| 2003/0096011 A1 | 5/2003 | Tracy |
| 2003/0099964 A1 | 5/2003 | Patil et al. |
| 2003/0220777 A1 | 11/2003 | Kitchen et al. |
| 2005/0042668 A1 | 2/2005 | Perlin |
| 2005/0086035 A1 | 4/2005 | Peccoud et al. |
| 2005/0250125 A1 | 11/2005 | Novakoff |
| 2005/0260645 A1 | 11/2005 | Green et al. |
| 2006/0184489 A1 | 8/2006 | Weiner et al. |
| 2006/0278241 A1 | 12/2006 | Ruano |
| 2007/0111247 A1 | 5/2007 | Stephens et al. |
| 2007/0184436 A1 | 8/2007 | Myerson et al. |
| 2009/0026082 A1 | 1/2009 | Rothberg et al. |
| 2009/0029364 A1 | 1/2009 | Zirwes et al. |
| 2009/0127589 A1 | 5/2009 | Rothberg et al. |
| 2009/0183268 A1 | 7/2009 | Kingsmore et al. |
| 2009/0191565 A1 | 7/2009 | Lapidus et al. |
| 2009/0326832 A1 | 12/2009 | Heckerman et al. |
| 2010/0029498 A1 | 2/2010 | Gnirke et al. |
| 2010/0035252 A1 | 2/2010 | Rothberg et al. |
| 2010/0042438 A1 | 2/2010 | Moore et al. |
| 2010/0137143 A1 | 6/2010 | Rothberg et al. |
| 2010/0145981 A1* | 6/2010 | Wojcicki ............... G16B 20/40 707/769 |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009296 A1 | 1/2011 | Kain et al. |
| 2011/0184896 A1 | 7/2011 | Guyon |
| 2012/0058480 A1 | 3/2012 | Lewis et al. |
| 2012/0077682 A1 | 3/2012 | Bowcock et al. |
| 2012/0116688 A1 | 5/2012 | Bhubaneswar et al. |
| 2012/0143512 A1 | 6/2012 | Reese et al. |
| 2012/0270206 A1 | 10/2012 | Ginns et al. |
| 2013/0073217 A1 | 3/2013 | Dewey et al. |
| 2013/0090908 A1 | 4/2013 | Dewey et al. |
| 2013/0096011 A1 | 4/2013 | Rava et al. |
| 2013/0124100 A1 | 5/2013 | Drmanac et al. |
| 2013/0173177 A1 | 7/2013 | Pelleymounter |
| 2013/0178389 A1 | 7/2013 | Lapidus et al. |
| 2013/0296535 A1 | 11/2013 | Church et al. |
| 2013/0311448 A1* | 11/2013 | Thompson ............ G06F 16/902 707/E17.014 |
| 2013/0332081 A1* | 12/2013 | Reese ................. G16B 20/20 702/19 |
| 2014/0200147 A1 | 7/2014 | Bartha et al. |
| 2015/0051087 A1 | 2/2015 | Rabinowitz et al. |
| 2015/0057160 A1 | 2/2015 | Breuer et al. |
| 2016/0019341 A1 | 1/2016 | Harris et al. |
| 2016/0032396 A1 | 2/2016 | Diehn et al. |
| 2016/0041987 A1* | 2/2016 | Lapir .................. G06F 16/93 707/749 |

(56) References Cited

U.S. PATENT DOCUMENTS

| | | | |
|---|---|---|---|
| 2016/0092631 | A1 | 3/2016 | Yandell et al. |
| 2016/0283484 | A1 | 9/2016 | Chandratillake et al. |

FOREIGN PATENT DOCUMENTS

| | | |
|---|---|---|
| EP | 2861788 B1 | 10/2018 |
| WO | WO-2000018957 A1 | 4/2000 |
| WO | WO 2005098046 A2 | 10/2005 |
| WO | WO-2007055244 A1 | 5/2007 |
| WO | WO 2010054589 A1 | 5/2010 |
| WO | WO-2011050341 A1 | 4/2011 |
| WO | WO-2011057061 A1 | 5/2011 |
| WO | WO-2011057094 A1 | 5/2011 |
| WO | WO-2011091046 A1 | 7/2011 |
| WO | WO-2011160063 A2 | 12/2011 |
| WO | WO-2011160206 A1 | 12/2011 |
| WO | WO-2012142611 A2 | 10/2012 |
| WO | WO-2014053295 A1 | 4/2014 |
| WO | WO-2014113204 A1 | 7/2014 |
| WO | WO-2014207245 A1 | 12/2014 |
| WO | WO-2015051275 A1 | 4/2015 |

OTHER PUBLICATIONS

Choi, et al. Genetic diagnosis by whole exome capture and massively parallel DNA sequencing. Proc Natl Acad Sci U S A. Nov. 10, 2009;106(45):19096-101. doi: 10.1073/pnas.0910672106. Epub Oct. 27, 2009.

Co-pending U.S. Appl. No. 15/929,318, inventors Chandratillakegemma; L. et al., filed Apr. 24, 2020.

Co-pending U.S. Appl. No. 16/255,762, inventors Chandratillakegemma; L. et al., filed Jan. 23, 2019.

Co-pending U.S. Appl. No. 16/570,219, inventors Chandratillakegemma; L. et al., filed Sep. 13, 2019.

International search report and written opinion dated Jan. 8, 2015 for PCT Application No. US2014/059103.

Ng, et al. Targeted capture and massively parallel sequencing of 12 human exomes. Nature. Sep. 10, 2009;461(7261):272-6. doi: 10.1038/nature08250. Epub Aug. 16, 2009.

Singleton, et al. Phevor combines multiple biomedical ontologies for accurate identification of disease-causing alleles in single individuals and small nuclear families. Am J Hum Genet. Apr. 3, 2014;94(4):599-610. doi: 10.1016/j.ajhg.2014.03.010.

SVBio's services, http://www.svbio.com/service-offerings/current-services. Accessed Oct. 1, 2014.

U.S. Appl. No. 15/083,058 Notice of Allowance dated Dec. 10, 2018.

U.S. Appl. No. 15/083,058 Notice of Allowance dated Feb. 6, 2019.

U.S. Appl. No. 15/083,058 Office Action dated Mar. 21, 2018.

Van Driel, et al. A text-mining analysis of the human phenome. Eur J Hum Genet. May 2006;14(5):535-42.

Adessi, et al. Solid phase DNA amplification: characterisation of primer attachment and amplification mechanisms. Nucleic Acids Res. Oct. 15, 2000;28(20):E87.

Albert, et al. Direct selection of human genomic loci by microarray hybridization. Nat Methods. Nov. 2007;4(11):903-5. Epub Oct. 14, 2007.

Asan, et al. Comprehensive comparison of three commercial human whole-exome capture platforms. Genome Biol. Sep. 28, 2011;12(9):R95. doi: 10.1186-gb-2011-12-9-r95.

Ausubel, et al. eds. Current Protocols in Molecular Biology. United States. Greene Publishing Associates and Wiley-Interscience. 1987. (Table of Contents).

Baingridge, et al. Whole exome capture in solution with 3 Gbp of data. Genome Biol. 2010;11(6):R62. doi: 10.1186-gb-2010-11-6-r62. Epub Jun. 17, 2010.

Baird, et al. Developing recombinant antibodies for biomarker detection. Cancer Biomark. 2010;6(5-6):271-9. doi: 10.3233-CBM-2009-0144.

Bamshad., "Exome sequencing as a tool for Mendelian disease gene discovery", Nature Reviews Genetics, Nov. 2011, 12, 745-755.

Beck, et al. Profile of the circulating DNA in apparently healthy individuals. Clin Chem. Apr. 2009;55(4):730-8. doi: 10.1373-clinchem.2008.113597. Epub Jan. 30, 2009.

Benesova et al., "Mutation-based detection and monitoring of cell-free tumor Dna in peripheral blood of cancer patients", Analytical Biochemistry vol. 433, Issue 2, Feb. 15, 2013, pp. 227-234.

Bent, et al., "Enriching pathogen transcripts from infected samples: A capture-based approach to enhanced host-pathogen RNA sequencing", Analytical Biochemistry, Jul. 1, 2013; vol. 438, No. 1, pp. 90-96, XP055220731, DOI: 10.1016-j.ab.2013.03.008. * abstract; pp. 91-92 "Material and Methods" *.

Biesecker, et al. A genomic view of mosaicism and human disease. Nat Rev Genet. May 2013;14(5):307-20. doi: 10.1038-nrg3424.

Bischoff, et al. Cell-free fetal DNA and intact fetal cells in maternal blood circulation: implications for first and second trimester non-invasive prenatal diagnosis. Hum Reprod Update. Nov.-Dec. 2002;8(6):493-500.

Blanco et al., "Highly Efficient DNA Synthesis by the Phage phi 29 DNA polymerase", Journal of Biological Chemistry, vol. 264, No. 15, pp. 8935-8940, May 25, 1989.

Blaschko. The nerve distribution in the skin in their relation to the diseases of the skin: a report to the VII Congress of the German Society of Dermatology, held at Wroclaw 28-30. May 1901. (in German with English abstract).

Boers et al., "High-Throughput Multilocus Sequence Typing: Bringing Molecular Typing to the Next Level," PLoS One 2012; 7(7):e39630.

Bonadona, et al. Cancer risks associated with germline mutations in MLH1, MSH2, and MSH6 genes in Lynch syndrome. JAMA. Jun. 8, 2011;305(22):2304-10. doi: 10.1001-jama.2011.743.

Boulesteix, et al. Evaluating microarray-based classifiers: an overview. Cancer Inform. 2008;6:77-97. Epub Feb. 29, 2008.

Braslavsky, et al. Sequence information can be obtained from single DNA molecules. Proc Natl Acad Sci USA. Apr. 1, 2003;100(7):3960-4. Epub Mar. 21, 2003.

Browne, et al. Increased promoter methylation in exfoliated breast epithelial cells in women with a previous breast biopsy. Epigenetics. Dec. 2011;6(12):1425-35. doi: 10.4161-epi.6.12.18280.

Bryzgunova, et al. Isolation and comparative study of cell-free nucleic acids from human urine. Ann NY Acad Sci. Sep. 2006;1075:334-40.

Carlson, et al. Decoding cell lineage from acquired mutations using arbitrary deep sequencing. Nat Methods. Nov. 27, 2011;9(1):78-80. doi: 10.1038-nmeth.1781.

Chang, et al., Role of Bacteria in Oncogenesis. Clinical Microbiology Reviews, Oct. 2010; vol. 23 No. 4: p. 837-857.

Chiu, et al. Effects of blood-processing protocols on fetal and total DNA quantification in maternal plasma. Clin Chem. Sep. 2001;47(9):1607-13.

Clark, et al. Performance comparison of exome DNA sequencing technologies. Nat Biotechnol. Sep. 25, 2011;29(10):908-14. doi: 10.1038-nbt.1975.

Craig, et al. Identification of genetic variants using bar-coded multiplexed sequencing. Nat Methods. Oct. 2008;5(10):887-93. Epub Sep. 14, 2008.

Damani, et al. Characterization of circulating endothelial cells in acute myocardial infarction. Sci Transl Med. Mar. 21, 2012 ;4(126):126ra33. doi: 10.1126-scitranslmed.3003451.

Dawe, et al. Cell migration from baby to mother. Cell Adh Migr. Jan.-Mar. 2007;1(1):19-27. Epub Jan. 28, 2007.

De La Chapelle. The incidence of Lynch syndrome. Fam Cancer. 2005;4(3):233-7.

De Mattos-Aruda et al., Circulating tumor cells and cell-free DNA as tools for managing breast cancer, Nat. Rev. Clin. Oncol 10, 377-389 (2013); published online May 28, 2013 doi:10.1038-nrclinonc.2013.80.

De Cathelineau, et al. The final step in programmed cell death: phagocytes carry apoptotic cells to the grave. Essays Biochem. 2003;39:105-17.

(56) References Cited

OTHER PUBLICATIONS

Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al., "Human Genome Sequencing Using Unchained Base Reads on Self-Assembling DNA Nanoarrays", Science, 327(5961), pp. 78-81, Nov. 5, 2009.
Ellinger et al., "The role of cell-free circulating DNA in the diagnosis and prognosis of prostate cancer", Urologic Oncology 29:124-129 (2009), 124-129.
Elsharawy et al., "Accurate variant detection across non-amplified and whole genome amplified DNA using targeted next generation sequencing", BMC Genomics 13(500), pp. 1-14, Sep. 20, 2012.
Elshimali, et al. The clinical utilization of circulating cell free DNA (CCFDNA) in blood of cancer patients. Int J Mol Sci. Sep. 13, 2013;14(9):18925-58. doi: 10.3390-ijms140918925.
Fahy, et al. Self-sustained sequence replication (3SR): an isothermal transcription-based amplification system alternative to PCR. PCR Methods Appl. Aug. 1991;1 (1):25-33.
Fishel, et al. Meta-analysis of gene expression data: a predictor-based approach. Bioinformatics. Jul. 1, 2007;23(13):1599-606. Epub Apr. 26, 2007.
Freshney. Culture of Animal Cells: A Manual of Basic Technique and Specialized Applications. 6th Edition. 2010.
Frumkin, et al. Genomic variability within an organism exposes its cell lineage tree. PLoS Comput Biol. Oct. 2005;1 (5):e50. Epub Oct. 28, 2005.
Gnirke, et al. Solution Hybrid Selection with Ultra-long Oligonucleotides for Massively Parallel Targeted Sequencing. Nat. Biotechnol. (Feb. 1, 2009), 27(2):182-9.
Golob, Mechanisms of cell fate acquisition in the differentiation of pluripotent stem cells. Dissertation. University of Washington. 2009; 110 pages.
Goris; et al., "The Immunogenetic Architecture of Autoimmune Disease", Cold Spring Harbor Perspectives in Biology, 2012, 4:a007260, 1-15.
Gottlieb, et al. The DiGeorge syndrome minimal critical region contains a goosecoid-like (GSCL) homeobox gene that is expressed early in human development. Am J Hum Genet. May 1997;60(5):1194-201.
Guo et al., "Exome sequencing generates high quality data in non-target regions", BMC Genomics 13(194), pp. 1-10, May 20, 2012. Main text.
Guo et al., "Exome sequencing generates high quality data in non-target regions", BMC Genomics 13(194), pp. 1-10, May 20, 2012. Supplementary Tables.
Hamfjord et al., Plos ONE at www.plosone.org Apr. 2012, vol. 7, Issue 4, e34150.
Hiratani, et al., Replication timing and transcriptional control: beyond cause and effect—part II. Curr Opin Genet Dev. Apr. 2009;19(2):142-9. doi: 10.1016-j.gde.2009.02.002. Epub Apr. 1, 2009.
Hirschhorn, et al. Human intersex with chromosome mosaicism of type XY-XO. Report of a case. N Engl J Med. Nov. 24, 1960;263:1044-8.
Huang, et al. Characterization of human plasma-derived exosomal RNAs by deep sequencing. BMC Genomics. May 10, 2013;14:319. doi: 10.1186-1471-2164-14-319.
Human Genome Overview GRCh37. Genome Reference Consortium, Feb. 27, 2009. 1 Page.
Human Genome Overview GRCh37.p13. Genome Reference Consortium, Jun. 28, 2013. 2 Pages.
Illumina., "Interpreting Infinium Assay Data for Whole-Genome Structural Variation", Technical Note: DNA Analysis, 2010. Website, 1-8.
Jung et al., "Cell-free DNA in the blood as a solid tumor biomarker—A critical appraisal of the literature", Clinica Chimica Acta 411 :1611-1624 (2010).
Karam, et al. Apoptosis in Carcinogenesis and Chemotherapy. Published by Springer in 2009 ISBN: 978-1-4020-9596-2.
Kiialainen, et al. Performance of microarray and liquid based capture methods for target enrichment for massively parallel sequencing and SNP discovery. PLoS One. Feb. 9, 2011;6(2):e16486. doi: 10.1371-journal.pone.0016486.
Kinde, et al. Detection and quantification of rare mutations with massively parallel sequencing. Proc Natl Acad Sci US A. Jun. 7, 2011;108(23):9530-5. doi: 10.1073-pnas.1105422108. Epub May 17, 2011.
Koboldt et al., "VarScan: variant detection in massively parallel sequencing of individual and pooled samples", Bioinformatics, 25(17), pp. 2283-2285, Jun. 19, 2009.
Kokawa, et al. Apoptosis in the human uterine endometrium during the menstrual cycle. J Clin Endocrinol Metab. Nov. 1996;81 (11):4144-7.
Koren, et al. Differential relationship of DNA replication timing to different forms of human mutation and variation. Am J Hum Genet. Dec. 7, 2012;91 (6):1033-40. doi: 10.1016-j.ajhg.2012.10.018. Epub Nov. 21, 2012.
Krumm et al., "Copy number variation detection and genotyping from exome sequence data", Genome Research, 22(8), pp. 1525-1532, May 14, 2012.
Kuchler, et al. Buccal cells DNA extraction to obtain high quality human genomic DNA suitable for polymorphism genotyping by PCR-RFLP and Real-Time PCR. J Appl Oral Sci. Jul.-Aug. 2012;20(4):467-71.
Laktionov et al. "Cell-surface-bound nucleic acids: Free and cell-surface-bound nucleic acids in blood of healthy donors and breast cancer patients", Ann. NY Acad Sci 1022:221-227 (2004).
Lam, et al. Time course of early and late changes in plasma DNA in trauma patients. Clin Chem. Aug. 2003;49(8):1286-91.
Larson et al., "SomaticSniper: identification of somatic point mutations in whole genome sequencing data", Bioinformatics, 28(3), pp. 311-317, Dec. 6, 2011.
Lathe, R., Synthetic oligonucleotide probes deduced from amino acid sequence data: Theoretical and practical considerations. Journal of Molecular Biology, May 5, 1985; 183(1): 1-12.
Leamon, et al. A massively parallel PicoTiterPlate based platform for discrete picoliter-scale polymerase chain reactions. Electrophoresis. Nov. 2003; 24(21):3769-77.
Leary, et al. Detection of chromosomal alterations in the circulation of cancer patients with whole genome-sequencing. Sci Transl Med. Nov. 28, 2012;4(162):162ra154. doi: 10.1126-scitranslmed.3004742.
Levin, et al., Targeted next-generation sequencing of a cancer transcriptome enhances detection of sequence variants and novel fusion transcripts. Genome Biology, 2009. 10:R115.
Li et al., "The Sequence Alignment/MAP format and SAMtools", Bioinformatics, 25(16), pp. 2078-2079, Jun. 8, 2009.
Li, et al., "Novel computational methods for increasing PCR primer design effectiveness in directed sequencing", BMC Bioinformatics. Apr. 11, 2008;9:191. doi: 10.1186-1471-2105-9-191.
Lizardi, et al. Mutation detection and single-molecule counting using isothermal rolling-circle amplification. Nat Genet. Jul. 1998;19(3):225-32.
Lo et al., "Presence of fetal DN in maternal plasma and serum", Lancet 1997 350 485-87.
Lo, et al. Rapid clearance of fetal DNA from maternal plasma. Am J Hum Genet. Jan. 1999;64(1):218-24.
Madeleine et al., "Comprehensive Analysis of HLA-A, HLA-B, HLA-C, HLA-DRB1, and HLA-DQB1 Loci and Squamous Cell Cervical Cancer Risk", Cancer Res 2008; 68 (9), May 1, 2008.
Maluf et al., The Urine microRNA profile may help profile may help monitor post-transplant renal graft function, Kidney International. Published online Sep. 11, 2013; vol. 85. No. 2: pp. 439-449. XP055442385.
Margulies, et al. Genome sequencing in microfabricated high-density picolitre reactors. Nature. Sep. 15, 2005;437(7057):376-80. Epub Jul. 31, 2005.
Market, et al., V(D)J Recombination and the Evolution of the Adaptive Immune System. Plos Biol. 2003; 1(1):e16. https:--doi.org-10.1371-journal.pbio.0000016.

(56) References Cited

OTHER PUBLICATIONS

Marsh. Pyrosequencing applications. Methods Mol Biol. 2007;373:15-24.
Masuzaki, et al. Detection of cell free placental DNA in maternal plasma: direct evidence from three cases of confined placental mosaicism. J Med Genet. Apr. 2004; 41 (4):289-92.
Michaelson, et al. Whole-genome sequencing in autism identifies hot spots for de novo germline mutation. Cell. Dec. 21, 2012;151(7):1431-42. doi: 10.1016-j.cell.2012.11.019.
Miller, et al., Basic concepts of microarrays and potential applications in clinical microbiology. Clinical Microbiology Reviews, Oct. 2009, p. 611-633.
Mitra, et al. In situ localized amplification and contact replication of many individual DNA molecules. Nucleic Acids Res. Dec. 15, 1999;27(24):e34.
Moudrianakis, et al. Base sequence determination in nucleic acids with the electron microscope. 3. Chemistry and microscope of guanine-labeled DNA. Proc Natl Acad Sci U S A. Mar. 1965;53:564-71.
Muniappan, et al. The DNA polymerase beta replication error spectrum in the adenomatous polyposis coli gene contains human colon tumor mutational hotspots. Cancer Res. Jun. 1, 2002; 62(11):3271-5.
Murray, et al., Improved double-stranded DNA sequencing using the linear polymerase chain reaction. Nucleic Acids Research, vol. 17, No. 21. p. 8889. Nov. 11, 1989.
Ng et al., "Exome sequencing identifies the cause of a mendelian disorder", Nature Genetics, 42(1), pp. 30-35, Nov. 13, 2009.
Nucleosome Position by MNase-seq from ENCODE-Stanford-BYU. track settings from the UC Santa Cruz Genome Browser. 2011-2012. http:--hgdownload.cse.ucsc.edu-goldenPath-hg19-encodeDCC-wgEncodeSydhNsome-.
Ochman, et al. Genetic applications of an inverse polymerase chain reaction. Genetics. Nov. 1988;120(3):621-3.
Ozsolak, et al. Direct RNA sequencing. Nature. Oct. 8, 2009;461(7265):814-8. doi: 10.1038-nature08390. Epub Sep. 23, 2009.
Park. Scientists Devise a Blood Test to Predict Heart Attack. Time Magazine. Mar. 22, 2012. 2 pages.
Pasaniuc, et al. Extremely low-coverage sequencing and imputation increases power for genome-wide association studies. Nat Genet. May 20, 2012;44(6):631-5. doi: 10.1038-ng.2283. With Supplementary Information.
Pierce, et al. Linear-after-the-exponential polymerase chain reaction and allied technologies. Real-time detection strategies for rapid, reliable diagnosis from single cells. Methods Mol Med. 2007;132:65-85.
Pritchard et al., "ColoSeq Provides Comprehensive Lynch and Polyposis Syndrome Mutational Analysis Using Massively Parallel Sequencing", Journal of Molecular Diagnostics, vol. 14, No. 4, Jul. 2012.
Punnoose, et al. Molecular biomarker analyses using circulating tumor cells. PLoS One. Sep. 8, 2010;5(9):e12517. doi: 10.1371-journal.pone.0012517.
Richter. Fecal DNA screening in colorectal cancer. Can J Gastroenterol. Jul. 2008;22(7):631-3.
Robinson, et al. Strategies for exome and genome sequence data analysis in disease gene discovery projects. Clinical Genetics, vol. 80, No. 2, pp. 127-132 (2011) See the whole document.
Robinson; et al., "The Human Phenotype Ontology: A Tool for Annotating and Analyzing Human Hereditary Disease", The American Journal of Human Genetics, Nov. 7, 2008, 83, 610-615.
Rogozin, et al. Somatic mutation hotspots correlate with DNA polymerase eta error spectrum. Nat Immunol. Jun. 2001;2(6):530-6.
Rosenfeld, et al. Novel multi-nucleotide polymorphisms in the human genome characterized by whole genome and exome sequencing. Nucleic Acids Research, Article No. gkq408, pp. 1-10 (2010) See abstract; and pp. 8-9.
Ross, et al. Characterizing and measuring bias in sequence data. Genome Biology, vol. 14, No. 5, Article No. R51, pp. 1-20 (e-pub, May 29, 2013) See the whole document.
Ross. Introduction to Oncogenes and Molecular Cancer Medicine. Copyright 1998 Springer-Verlag New York, Inc. ISBN : 0-387-98392-9.
Saeys, et al. A review of feature selection techniques in bioinformatics. Bioinformatics. Oct. 1, 2007;23(19):2507-17. Epub Aug. 24, 2007.
Saiki, et al. Analysis of enzymatically amplified beta-globin and HLA-DQ alpha DNA with allelespecific oligonucleotide probes. Nature. Nov. 13-19, 1986;324(6093):163-6.
Sambrook, et al. Molecular Cloning: A Laboratory Manual. 4th Edition, 2012.
Sandri, et al. Apoptosis, DNA damage and ubiquitin expression in normal and mdx muscle fibers after exercise. FEBS Lett. Oct. 16, 1995;373(3):291-5.
Schmitt, et al. Detection of ultra-rare mutations by next-generation sequencing. Proc Natl Acad Sei US A. Sep. 4, 2012;109(36):14508-13. doi: 10.1073-pnas.1208715109. Epub Aug. 1, 2012.
Schwarzenbach, et al. Detection and monitoring of cell-free DNA in blood of patients with colorectal cancer. Ann NY Acad Sci. Aug. 2008;1137:190-6. doi: 10.1196-annals.1448.025.
Shaw et al. Genomic analysis of circulating cell-free DNA infers breast cancer dormancy. Genome Research 22(2):220-231 (Feb. 2012).
Shigemizu et al., "A practical method to detect SNVs and indels from whole genome and exome sequencing data", Scientific Reports, 3(1), pp. 1-6, Jul. 8, 2013. Main Text.
Shigemizu et al., "A practical method to detect SNVs and indels from whole genome and exome sequencing data", Scientific Reports, 3(1), pp. 1-6, Jul. 8, 2013; Supplementary Information.
Smyth. Limma: linear models for microarray data. In: Bioinformatics and Computational Biology Solutions using R and Bioconductor. R. Gentleman, V. Carey, S. Dudoit, R. Irizarry, W. Huber (eds.), 2007, Springer, New York, pp. 397-420.
Soni, et al. Progress toward ultrafast DNA sequencing using solid-state nanopores. din Chem. Nov. 2007;53(11):1996-2001. Epub Sep. 21, 2007.
Spalding, et al. Retrospective birth dating of cells in humans. Cell. Jul. 15, 2005;122(1):133-43.
Stemmer, et al. Single-step assembly of a gene and entire plasmid from large numbers of oligodeoxyribonucleotides. Gene. Oct. 16, 1995; 164(1):49-53.
Sulston, et al. Post-embryonic cell lineages of the nematode, Caenorhabditis elegans. Dev Biol. Mar. 1977;56(1):110-56.
Sulston, et al. The embryonic cell lineage of the nematode Caenorhabditis elegans. Dev Biol. Nov. 1983;100(1):64-119.
Teer et al., "Exome sequencing: the sweet spot before whole genomes", Human Molecular Genetics, 19(R2), R145-R151, Aug. 12, 2010.
Tewhey, et al. Microdroplet-based PCR enrichment for large-scale targeted sequencing. Nat Biotechnol. Nov. 2009;27(11):1025-31. doi: 10.1038-nbt.1583. Epub Nov. 1, 2009.
The Human Cell Lineage Flagship Initiative. Last updated Nov. 10, 2010. 1 page. http:--www. lineage-flagsh ip.eu-.
Turajilic et al., "Whole genome sequencing of matched primary and metastatic acral melanomas", Genome Research, 22(2), pp. 196-207, Feb. 22, 2012. Main document.
Turajilic et al., "Whole genome sequencing of matched primary and metastatic acral melanomas", Genome Research, 22(2), pp. 196-207, Feb. 22, 2012. Supplementary Figures.
Turajilic et al., "Whole genome sequencing of matched primary and metastatic acral melanomas", Genome Research, 22(2), pp. 196-207, Feb. 22, 2012. Supplementary Tables.
Valadi, et al. Exosome-mediated transfer of mRNAs and microRNAs is a novel mechanism of genetic exchange between cells. Nat Cell Biol. Jun. 2007;9(6):654-9. Epub May 7, 2007.
VarScan. (2009). Retrieved from http:--varscan.sourceforge.net-.
Vasan, Biomarkers of cardiovascular disease: molecular basis and practical considerations. Circulation. May 16, 2006;113(19):2335-62.

(56) References Cited

OTHER PUBLICATIONS

Velculescu, et al. Characterization of the yeast transcriptome. Cell. Jan. 24, 1997;88(2):243-51.
Velculescu, et al. Serial analysis of gene expression. Science. Oct. 20, 1995;270(5235):484-7.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995; 23(21):4407-14.
Walker, et al. Strand displacement amplification—an isothermal, in vitro DNA amplification technique. Nucleic Acids Res. Apr. 11, 1992 ;20(7):1691-6.
Wang, K. (2010). Annovar Documentation. Retrieved from http:--annovar.openbioinformatics.org-.
Warren, R.L. et al., Targeted assembly of short sequence reads. PLOS One, 6(5): May 5, 2011; p. e19816, XP055347747, DOI:10.1371-journal.pone-0019816.
Wasserstrom, et al. Reconstruction of cell lineage trees in mice. PLoS One. Apr. 9, 2008;3(4):e1939. doi: 10.1371-journal.pone.0001939.
Westin, et al. Anchored multiplex amplification on a microelectronic chip array. Nat Biotechnol. Feb. 2000;18(2):199-204.
Xiao, et al. Identifying mRNA, microRNA and protein profiles of melanoma exosomes. PLoS One. 2012;7(10):e46874. doi: 10.1371-journal.pone.0046874. Epub Oct. 9, 2012.
Yeung et al., "LOH in the HLA Class I Region at 6p21 is Associated with Shorter Survival in Newly Diagnosed Glioblastoma", Clinical Cancer Research, pp. 1816-1826, Apr. 1, 2013.
Yi et al., "Sequencing of Fifty Human Exomes Reveals Adaptation to High Altitude", Science, 329(5987), pp. 75-78, Jul. 2, 2010.
Zeerleder. The struggle to detect circulating DNA. Crit Care. 2006;10(3):142. Epub May 16, 2006.
Akey et al., "Haplotypes vs. single marker linkage disequilibrium tests: what do we gain?", European Journal of Human Genetics, Apr. 20, 2001, vol. 8, pp. 291-300.
Anderson et al., "Next Generation DNA Sequencing and the Future of Genomic Medicine", Genes 2010, 38-69; doi:10.3390/genes1010038.
Chan et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry 59:1, 211-224 (2013).
Chu, Tianjiao et al., "Statistical model for whole genome sequencing and its application to minimally invasive diagnosis of fetal genetic disease", Bioinformatics, vol. 25, No. 10, 2009, pp. 1244-1250.
Forshew et al., "Noninvasive Identification and Monitoring of Cancer Mutations by Targeted Deep Sequencing of Plasma DNA", Science Translational Medicine, May 30, 2012, vol. 4, Issue 136, 136ra68; DOI: 10.1126/scitranslmed.3003726.
Forshew et al., "Noninvasive Identification and Monitoring of Cancer Mutations by Targeted Deep Sequencing of Plasma DNA", Supplementary Materials, Science Translational Medicine, May 30, 2012, vol. 4, Issue 136, 136ra68; DOI: 10.1126/scitranslmed.3003726.
Guo et al., "Whole-genome and whole-exome sequencing of bladder cancer identifies frequent alterations in genes involved in sister chromatid cohesion and segregation", nature Genetics, Letters, vol. 45, No. 12, Dec. 2013. Published online Oct. 13, 2013.
Leary et al., "Development of Personalized Tumor Biomarkers Using Massively Parallel Sequencing", Science Translational Medicine, Feb. 24, 2010; 2(20): 20ra14.
Ley et al., "DNA Sequencing of a cytogenetically normal acute myeloid leukemia genome", Nature, vol. 456|6 Nov. 2008.
Liao et al., "Targeted Massively Parallel Sequencing of Maternal Plasma DNA Permits Efficient and Unbiased Detection of Fetal Alleles", Clinical Chemistry 57:1, 92-101 (2011).
Mamanova et al., "Target-enrichment strategies for next-generation sequencing", Nature Methods, vol. 7, No. 2, Feb. 2010.
Mertes et al., "Targeted enrichment of genomic DNA regions for next-generation sequencing", Briefings in Functional Genomics, vol. 10, No. 6, 374-386, Nov. 26, 2011.
Podlaha, Ondrej et al., "Evolution of the cancer genome", Trends Genet. Apr. 2012 ; 28(4): 155-163. doi:10.1016/j.tig.2012.01.003.
Swanton, Charles, "Plasma-derived Tumor DNA Analysis at Whole-Genome Resolution," Editorials, Clinical Chemistry 59:1, 6-8; 2013.
Wagle, Nikhil et al., "High-Throughput Detection of Actionable Genomic Alterations in Clinical Tumor Samples by Targeted, Massively Parallel Sequencing", Cancer Discovery, Jan. 2012.
Yang, Yaping et al., "Clinical Whole-Exome Sequencing for the Diagnosis of Mendelian Disorders", New England Journal of Medicine, 369;16, Oct. 2, 2013.
Alter et al., "Clinical and molecular features associated with biallelic mutations in FANCD1/BRCA2," Journal of Medical Genetics 2007;44:1-9. doi: 10.1136/jmg.2006.043257.
Bentley, et al., "Accurate whole human genome sequencing using reversible terminator chemistry," Nature. Nov. 6, 2008; 456(7218): 53-59. doi:10.1038/nature07517.
Burrell et al., "The causes and consequences of genetic heterogeneity in cancer evolution" Nature. Sep. 19, 2013;501(7467):338-45. doi: 10.1038/nature12625.
Davies, et al., "Indications for Hematopoietic Cell Transplantation in Acute Leukemia," Biology of Blood and Marrow Transplantation 14:154-164 (2008). doi:10.1016/j.bbmt.2007.10.024.
Dawson, et al. "Analysis of Circulating Tumor DNA to Monitor Metastatic Breast Cancer," New England Journal of Medicine, 2013;368:1199-209; DOI:10.1056/NEJMoa1213261. Published online Mar. 13, 2013.
Haferlach et al., "Mutations of the TP53 gene in acute myeloid leukemia are strongly associated with a complex aberrant karyotype", Leukemia. Aug. 2008;22(8):1539-41. doi: 10.1038/leu.2008.143. Epub Jun. 5, 2008.
Misawa et al., "Significance of chromosomal alterations and mutations of the N-RAS and TP53 genes in relation to leukemogenesis of acute myeloid leukemia", Leuk Res. Jul. 1998;22(7):631-7. doi: 10.1016/s01452126(98)00056-3.
Newman et al., "An ultrasensitive method for quantitating circulating tumor DNA with broad patient coverage", Nat Med. May 2014 ; 20(5) 548-554. doi:10.1038/nm.3519.
Newman et al., "An ultrasensitive method for quantitating circulating tumor DNA with broad patient coverage", Nat Med. May 2014 ; 20(5) 548-554. Supplementary Excel Spreadsheets.
Vale et al., "Does anti-EGFR therapy improve outcome in advanced colorectal cancer? A systematic review and meta-analysis", Cancer Treatment Reviews 38 (2012) 618-625.

\* cited by examiner

METHODS FOR ANALYZING GENOTYPES

CROSS-REFERENCE

This application is a continuation application of U.S. patent application Ser. No. 15/929,318, filed Apr. 24, 2020, which is a continuation application of U.S. patent application Ser. No. 16/570,219, filed Sep. 13, 2019, which is a continuation application of U.S. patent application Ser. No. 16/255,762, filed Jan. 23, 2019, which is a continuation application of U.S. patent application Ser. No. 15/083,058, filed Mar. 28, 2016, now U.S. Pat. No. 10,255,330, which is a continuation application of International Patent Application No. PCT/US2014/059103, filed Oct. 3, 2014, which claims priority to U.S. Provisional Patent Application No. 61/886,555, filed Oct. 3, 2013, each of which are entirely incorporated herein by reference.

BACKGROUND

Genomic sequencing may generate vast troves of information that may be utilized for diagnosing a disease, or determining the genotypic causation of a diseases and/or trait. However, the shear amount of sequencing data may be difficult to navigate without reliance on certain assumptions and/or filters to minimize the amount of data to be searched. Assumptions and/or filters may prevent accurate assessment of sequencing data by either excluding important information that does not conform to expected assumptions and/or including too much information that impedes parsing the data.

SUMMARY

Provided herein are methods of ranking genotypes to allow consideration of variants with genotypes that do not conform to an expected or predetermined inheritance pattern, yet still facilitate prioritization of those that do. Such methods can be useful for facilitating causative variant discovery, diagnosis, and determining inheritance patterns of the genotypes.

In an aspect, the disclosure provides a computer-implemented method comprising receiving data relating to one or more phenotypes of a subject or family members, using a programmed computer processor, ranking a plurality of genes based at least in part on their association score with one or more phenotypes, and generating a numeric or graphical output with at least a subset of the plurality of genes ranked based on their association score with the one or more phenotypes.

In another aspect, the disclosure provides a computer-implemented method comprising receiving data relating to one or more genotypes of a subject or family members of the subject, receiving data relating to one or more phenotypes of the subject or family members of the subject, using a programmed computer processor ranking a plurality of genes of the one or more genotypes using an inheritance pattern score that is based on allowed genotypes with respect to the one or more phenotypes, and generating a numeric or graphical output with at least a subset of the plurality of genes ranked based on the inheritance pattern score. In another example, the disclosure provides a computer-implemented method comprising receiving data relating to one or more genotypes of a subject or family members of the subject, receiving data relating to one or more affected statuses of the subject or family members of the subject, using a programmed computer processor ranking a plurality of genes of the one or more genotypes using an inheritance pattern score that is based on allowed genotypes with respect to the one or more affected statuses, and generating a numeric or graphical output with at least a subset of the plurality of genes ranked based on the inheritance pattern score. The affected status can be one or more phenotypes of the subject or family members of the subject. Alternatively, the affected status can be the lack of one or more phenotypes of the subject or family members of the subject.

In another aspect, the disclosure provides a computer-implemented method comprising receiving data relating to one or more phenotypes of a subject or family members of the subject, receiving data relating to one or more genotypes of a subject or family members of the subject, using a programmed computer processor, ranking a plurality of genes based at least in part on their association score with one or more phenotypes, using the programmed computer processor, ranking the plurality of genes of the one or more genotypes using an inheritance pattern score that is based on allowed genotypes, and generating an output with at least a subset of the plurality of genes ranked based on the association score and inheritance pattern score.

In some embodiments, the one or more phenotypes comprise one or more diseases, traits, symptoms, laboratory values, diagnoses, behaviors, conditions, or a combination thereof. In some embodiments, the association score comprises the association of one or more genes with one or more of: genes, proteins, RNAs, pathognomonic features, clinical features, diseases, traits, symptoms, laboratory values, diagnoses, behaviors, conditions, differential diagnoses, prognoses, genetic history, familial information, hereditary information, human phenotypes, non-human phenotypes, genotypes, genomes, exomes, pathways, disease ontology, phenotype ontology, and gene ontology, or any combination thereof. In some embodiments, the association score represents a positive association. In some embodiments, the association score represents a neutral association. In some embodiments, the association score represents a negative association. In some embodiments, the association score is comprised of the combination of ranks of two or more genes. In some embodiments, ranking the data comprises ranking two or more genes. In some embodiments, the plurality of genes is ranked in computer memory. In some embodiments, ranking the two or more genes is based at least in part on the association score. In some embodiments, the plurality of genes are ranked substantially or entirely based on the association score. In some embodiments, the association score is related to the number of clinical features and/or diagnoses associated with the plurality of genes. In some embodiments, the association score is related to the number of clinical features and/or diagnoses associated with the two or more genes. In some embodiments, the association score is a weighted score. In some embodiments, the weighted score is based on (i) familial and/or hereditary information; (ii) specificity of a clinical feature-to-gene relationship; and/or (iii) reciprocity of clinical features and/or diseases associated with the genes. In some embodiments, the familial and/or hereditary information comprises the number of affected individuals in a family that is exhibiting a clinical feature and/or diagnosis. In some embodiments, the specificity of the clinical feature-to-gene relationship comprises pathognomonic features. In some embodiments, the output comprises a comparison of the data based on the association score that identifies the likelihood of one or more of: causative genes, neutral genes and non-causative genes. In some embodiments, the data comprises two or more genotypes. In some embodiments, the ranking comprises ranking the two or more genotypes. In some embodiments, the two or more genotypes are ranked based on the inheritance pattern score. In some embodiments, the inheritance pattern score is at least partially based on a likelihood of the genotype to explain a particular inheritance pattern, a segregation pattern, or a combination thereof. In some embodiments, the output is based on data from one or more databases that comprise one or more medical records, clinical notes, genomic databases, biomedical databases, clinical databases, scientific databases, disease databases, pathway and network databases, regulatory region databases, and biomarker databases, or any combination thereof. In some embodiments, the output is based on data from one or more databases or sources that comprise proprietary databases. In some embodiments, the output is based on data from one or more databases or sources that comprise publicly-available databases. In some embodiments, the publicly-available databases are selected from the group consisting of Orphanet, Human Phenotype Ontology (HPO), Online Mendelian Inheritance in Man (OMIM), Model Organism Gene Knock-Out databases, Kegg Disease Database, Reactome, BioCyc, WikiPathways, PID, Gene Ontology, ClinVar, COSMIC, Cancer Gene Census, RegulomeDB, miRbase, GAD, and GWAS Catalog, or any combination thereof. In some embodiments, the ranking is indicative of the likelihood of a genotype variant to be associated with a disease. In some embodiments, the data is first ranked by the inheritance pattern and then ranked by the association score. In some embodiments, the data is first ranked by the association score and then by the inheritance pattern. In some embodiments, the output is provided on an electronic display and/or stored in computer memory.

In some embodiments, the association score is generated by: generating, with the aid of a computer processor, a correlation between (i) one or more genes and (ii) a given phenotype or associated clinical feature among the one or more phenotypes or associated clinical features, to provide one or more sets of genes stored in a memory location, and designating each of the one or more sets of genes as (i) likely to be a causative of a given phenotype or associated clinical feature among the one or more phenotypes or associated clinical features if the given set of genes is associated with a plurality of search criteria (e.g., search terms) correlated with the given phenotype or associated clinical feature, (ii) neutral if the given set of genes is not associated with any phenotype or clinical feature, or (iii) unlikely to be causative of the given phenotype or clinical feature if the set of genes is associated with a plurality of phenotypes or associated clinical features that do not include the given phenotype or associated clinical feature. In some embodiments, the method further comprises ranking the one or more sets of genes based on the designating. In some embodiments, the method further comprises intersecting the one or more sets of genes with one or more variants of an individual or a family of the individual having a phenotype or associated clinical feature that is caused by, or is suspected to be caused by, one or more genetic variants. In some embodiments, the one or more variants are identified using a genetic sequencing system (e.g., Illumina®, Ion Torrent® or Pacific Biosciences® sequencer). In some embodiments, the data comprises clinical features. In some embodiments, the methods further comprise providing a diagnosis and/or treatment for the subject based on the output. In some embodiments, the methods further comprise diagnosing and/or treating the subject based on the output.

In some embodiments, the inheritance pattern score is generated by: generating, with the aid of a computer processor, one or more expected genotypes for all members of a family of the subject, wherein the one or more expected genotypes are generated for potential inheritance patterns of the family. In some embodiments, the method further comprises ranking the one or more expected genotypes based on a likelihood of an individual genotype among the one or more expected genotypes to provide a given inheritance pattern among the potential inheritance patterns. In some embodiments, the method further comprises analyzing a segregation pattern of a phenotype among the one or more phenotypes in the family. In some embodiments, the method further comprises determining a most likely inheritance pattern based on the segregation pattern of the phenotype. In some embodiments, the method further comprises ranking the one or more expected genotypes based on the most likely inheritance pattern. In some embodiments, the method further comprises identifying, with the aid of a genetic sequencing system, one or more genotypes of variants for one or more members of the family. In some embodiments, the method further comprises assigning a rank to each genotype of a given variant based on the rank of the corresponding genotype in the one or more expected genotypes. In some embodiments, the method further comprises using a programmed computer processor to correlate the genotype of a given variant that has a highest rank with at least a subset of the one or more phenotypes of the subject. In some embodiments, the method further comprises correlating the genotype of a given variant that has a highest rank with at least a subset of the one or more phenotypes of the subject.

In some embodiments, the data is related to the subject and one or more family members of the subject. In some embodiments, the data is related to the subject and two or more family members of the subject. In some embodiments, the output is in numeric or graphical form.

In some embodiments, the genetic sequencing system employs untargeted sequencing, a target-specific sequencing, or a combination thereof. In some embodiments, the genetic sequencing system is an untargeted sequencing, a target-specific sequencing or a combination thereof. In some embodiments, the genetic sequencing system is an untargeted sequencing, for example, a whole-genome sequencing. In some embodiments, the genetic sequencing system is a target-specific sequencing.

In another aspect, the present disclosure provides a computer system comprising computer memory storing data relating to one or more phenotypes of a subject or family members of the subject, and a computer processor that is programmed to (i) receive the data relating to the one or more phenotypes of the subject or family members of the subject, (ii) rank a plurality of genes based at least in part on their association score with the one or more phenotypes, and (iii) generate an output with at least a subset of the plurality of genes ranked based on their association score with the one or more phenotypes.

In another aspect, the present disclosure provides a computer system comprising computer memory storing data relating to one or more genotypes of a subject or family members of the subject and data relating to one or more phenotypes of the subject or family members of the subject, and a computer processor that is programmed to (i) receive the data relating to one or more genotypes of a subject or family members of the subject, (ii) receive the data relating to the one or more phenotypes of the subject or family members of the subject, (iii) rank a plurality of genes of the one or more genotypes using an inheritance pattern score that is based on allowed genotypes with respect to the one or more phenotypes, and (iv) generate an output with at least a subset of the plurality of genes ranked based on the inheritance pattern score.

In another aspect, the present disclosure provides a computer system comprising computer memory storing data relating to one or more phenotypes of a subject or family members of the subject and data relating to one or more genotypes of the subject or family members of the subject, and a computer processor that is programmed to (i) receive the data relating to one or more phenotypes of a subject or family members of the subject, (ii) receive the data relating to one or more genotypes of the subject or family members of the subject, (iii) rank a plurality of genes based at least in part on their association score with the one or more phenotypes, (iv) rank the plurality of genes of the one or more genotypes using an inheritance pattern score that is based on allowed genotypes, and (v) generate an output with at least a subset of the plurality of genes ranked based on the association score and inheritance pattern score.

In another aspect, the present disclosure provides a computer-readable medium comprising machine executable code that, upon execution by one or more computer processors, implements a method, wherein the method comprises receiving data relating to one or more phenotypes of a subject or family members of the subject, ranking a plurality of genes based at least in part on their association score with the one or more phenotypes, and generating an output with at least a subset of the plurality of genes ranked based on their association score with the one or more phenotypes.

In another aspect, the present disclosure provides a computer-readable medium comprising machine executable code that, upon execution by one or more computer processors, implements a method, wherein the method comprises receiving data relating to one or more genotypes of a subject or family members of the subject, receiving data relating to one or more phenotypes of the subject or family members of the subject, ranking a plurality of genes of the one or more genotypes using an inheritance pattern score that is based on allowed genotypes with respect to the one or more phenotypes, and generating an output with at least a subset of the plurality of genes ranked based on the inheritance pattern score.

In another aspect, the present disclosure provides a computer-readable medium comprising machine executable code that, upon execution by one or more computer processors, implements a method, wherein the method comprises receiving data relating to one or more phenotypes of a subject or family members of the subject, receiving data relating to one or more genotypes of the subject or family members of the subject, ranking a plurality of genes based at least in part on their association score with the one or more phenotypes, ranking the plurality of genes of the one or more genotypes using an inheritance pattern score that is based on allowed genotypes, and generating an output with at least a subset of the plurality of genes ranked based on the association score and inheritance pattern score.

In another aspect, the present disclosure provides a computer-readable medium comprising machine executable code that, upon execution by one or more computer processors, implements any of the methods above or elsewhere herein.

In another aspect, the present disclosure provides a computer system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
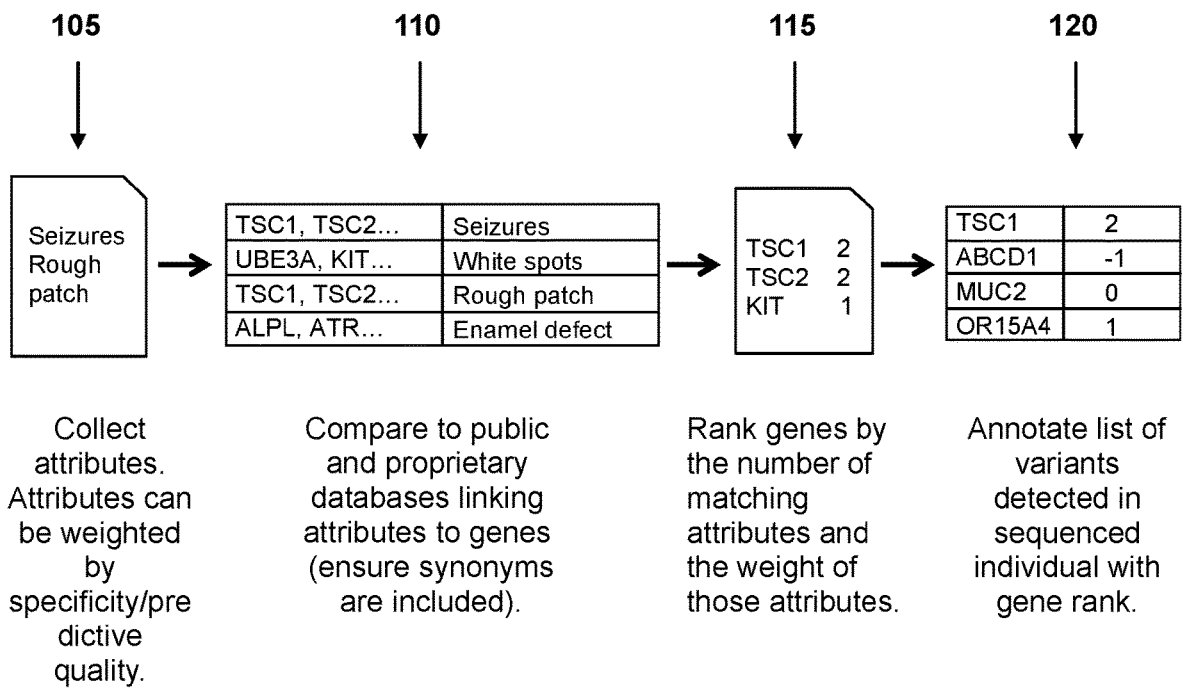
FIG. 1 illustrates an example of the feature-based ranking of genes (FROG) method of genotype analysis.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nucleic acid," as used herein, generally refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. A nucleic acid can refer to a polynucleotide. The backbone of the polynucleotide can comprise sugars and phosphate groups, as may typically be found in ribonucleic acid (RNA) or deoxyribonucleic acid (DNA), or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide can generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs can be derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule.

The terms "variant" and "derivative," as used herein in the context of a nucleic acid molecule, generally refer to a nucleic acid molecule comprising a polymorphism. Such terms can also refer to a nucleic acid product that is produced from one or more assays conducted on the nucleic acid molecule. For example, a fragmented nucleic acid molecule, hybridized nucleic acid molecule (e.g., capture probe hybridized nucleic acid molecule, bead bound nucleic acid molecule), amplified nucleic acid molecule, isolated nucleic acid molecule, eluted nucleic acid molecule, and enriched nucleic acid molecule are variants or derivatives of the nucleic acid molecule.

The term "subject," as used herein, generally refers to any organism that is used in the methods of the disclosure. In some examples, a subject is a human, mammal, vertebrate, invertebrate, eukaryote, archaea, fungus, or prokaryote. In some instances, a subject can be a human. A subject can be living or dead. A subject can be a patient. For example, a subject may be suffering from a disease (or suspected of suffering from a disease) and/or in the care of a medical practitioner. A subject can be an individual that is undergoing treatment and/or diagnosis for a health or medical condition. A subject and/or family member can be related to another subject used in the methods of the disclosure (e.g., a sister, a brother, a mother, a father, a nephew, a niece, an aunt, an uncle, a grandparent, a great-grandparent, a cousin).

The term "phenotype," as used herein, generally refers to a composite of characteristics or traits of a subject or family member of the subject, such as its morphology, development, biochemical or physiological properties, phenology, behavior and products of behavior. The characteristics or traits may be observable.

The term "affected status," as used herein, generally refers to the presence of or lack of one or more phenotypes in a subject and/or one or more family members of the subject. In an example, the affected status of a subject is depicted by way of a family tree that shows which family member(s) of the subject has a given phenotype (e.g., disease).

The term "rank" or "ranking" as used herein, generally refers to a method of listing data according to a classification. The classification may comprise comparing between different data points. The classification may comprise comparing between association scores and/or inheritance pattern genotype scores.

General Overview

The disclosure provides methods for analyzing genotype data that can originate from sequencing. Analyzing a genotype can include determining the likelihood of inheritance of the genotype, determining if the genotype is causative of a disease, and/or diagnosing a disease. In some instances, the methods of the disclosure provide for developing a subject-specific ontology profile. An ontology profile can comprise ontology for features (e.g., diseases, traits, phenotypes). The ontology profile can comprise ontology used to describe symptoms, diseases, phenotypes, hereditary information, genetic information, traits, prognoses, familial information, pathognomonic features and clinical features. The subject-specific ontology profile can be compared to database ontology profiles. Ontology profiles that match between the subject and the database can signify a similar genotype between the subject and the database. The matching database genotype can be retrieved and ranked according to an association score, wherein the ranking ranks the genotypes most likely to cause a disease as described by the subject-specific ontology profile. The association score can weight clinical features and diagnoses of the subject-specific ontology profile with diagnoses and/or clinical features of the same diseases in family members. The association score ranking can be equal to the sum of the weighted scores for each feature in the subject-specific ontology profile. In some instances, the ranking can account for reciprocity between the database profile and the subject-specific profile. For example, in some instances, the database ontology profile can retrieve an ontology feature which is not included in the subject-specific ontology profile. This can lead to changing the ranking of the genotype retrieved for the subject for that feature. In some instances, the weighting of genes in the ranking can take into account how specific the ontology features are. For example, if the ontology features are pathognomonic features, those genotypes can be ranked higher than if the features are merely correlative.

In some embodiments, the disclosure provides a method for analyzing genotype data that comprises generating an expected (or allowed) genotype of one or more subjects. The one or more subjects can be related to each other. Expected genotypes can be generated using clinical judgment and/or using Mendelian pattern expectations combined with known or presumed disease/phenotype penetrance values. For example, expected genotypes can be generated for a variety of inheritance patterns such as autosomal dominant, autosomal recessive, de novo dominant, inherited plus de novo recessive, inherited X-linked dominant, inherited X-linked recessive, de novo X-linked dominant, inherited plus de novo X-linked, inherited Y-linked, de novo Y-linked, inherited mitochondrial, de novo mitochondrial, and uniparental disomy. The expected genotypes can be ranked according to the likelihood of the inheritance patterns to be causative of the expected genotype. A phenotype within the one or more subjects can be identified and characterized according to a segregation pattern of the phenotype. The segregation pattern can determine which inheritance pattern is the most likely to explain the segregation of the phenotype. The expected genotypes can be ranked according to the most likely inheritance pattern. The ranked expected genotypes can be compared to real genotype data originating from sequencing. Genotypes that rank high against expected genotypes can be considered likely to be inherited according to the most likely inheritance pattern.

In some instances, the disclosure provides a method in which genotype data can be analyzed both by an association score and an inheritance pattern score. In some instances, the genotype data can be first analyzed by an association score and then analyzed by an inheritance pattern score. In some instances, the genotype data can first be analyzed by an inheritance pattern score and then by an association score. In some instances, the analysis (e.g., ranking can be displayed). The display can comprise a graphical form and/or a numerical form. The graphical form can comprise any graphical way to display data such as a bar graph and/or a pie chart. A numerical form can comprise any numerical way to display data such as a list.

Sequencing

In some instances, data to be analyzed by the methods of the disclosure can comprise sequencing data. Sequencing data can be obtained by a variety of techniques and/or sequencing platforms. Sequencing techniques and/or platforms broadly fall into at least two assay categories (i.e., for example, polymerase and/or ligase based) and/or at least two detection categories (i.e., for example, asynchronous single molecule and/or synchronous multi-molecule readouts).

In some instances massively parallel high throughput sequencing techniques can avoid molecular cloning in a microbial host (i.e., for example, transformed bacteria, such as E. coli) to propagate the DNA inserts. Massively parallel high throughput sequencing techniques can use in vitro clonal PCR amplification strategies to meet the molecular detection sensitivities of the current molecule sequencing technologies. Some sequencing platforms (e.g., Helicos Biosciences) can avoid amplification altogether and sequence single, unamplified DNA molecules. With or without clonal amplification, the available yield of unique sequencing templates can have a significant impact on the total efficiency of the sequencing process.

Sequencing can be performed by sequencing-by-synthesis (SBS) technologies. SBS can refer to methods for determining the identity of one or more nucleotides in a polynucleotide or in a population of polynucleotides, wherein the methods comprise the stepwise synthesis of a single strand of polynucleotide complementary to the template polynucleotide whose nucleotide sequence is to be determined. An oligonucleotide primer can be designed to anneal to a predetermined, complementary position of the sample template molecule. The primer/template complex can be presented with a nucleotide in the presence of a nucleic acid polymerase enzyme. If the nucleotide is complementary to the position on the sample template molecule that is directly adjacent to the 3' end of the oligonucleotide primer, then the polymerase can extend the primer with the nucleotide. Alternatively, the primer/template complex can be presented with all nucleotides of interest (typically adenine (A), guanine (G), cytosine (C), and thymine (T)) at once, and the nucleotide that is complementary to the position on the sample template molecule directly adjacent to the 3' end of the oligonucleotide primer can be incorporated. In either scenario, the nucleotides may be chemically blocked (such as at the 3'-O position) to prevent further extension, and may be deblocked prior to the next round of synthesis. Incorporation of the nucleotide can be detected by detecting the release of pyrophosphate (PPi), via chemiluminescence, or by use of detectable labels bound to the nucleotides. Detectable labels can include mass tags and fluorescent or chemiluminescent labels. The detectable label can be bound directly or indirectly to the nucleotides. In the case of fluorescent labels, the label may be excited directly by an external light stimulus, or indirectly by emission from a fluorescent (FRET) or luminescent (LRET) donor. After detection of the detectable label, the label can be inactivated, or separated from the reaction, so that it may not interfere or mix with the signal from a subsequent label. Label separation can be achieved, for example, by chemical cleavage or photocleavage. Label inactivation can be achieved, for example, by photobleaching.

Sequencing data can be generated by sequencing by a nanopore-based method. In nanopore sequencing, a single-stranded DNA or RNA molecule can be electrophoretically driven through a nano-scale pore in such a way that the molecule traverses the pore in a strict linear fashion. Because a translocating molecule can partially obstruct or blocks the nanopore, it can alter the pore's electrical properties. This change in electrical properties can be dependent upon the nucleotide sequence, and can be measured. The nanopore can comprise a protein molecule, or it can be solid-state. Very long read lengths can be achieved, e.g. thousands, tens of thousands or hundreds of thousands of consecutive nucleotides can be read from a single molecule, using nanopore-based sequencing.

Another method of sequencing suitable for use in the methods of the disclosure is pyrophosphate-based sequencing. In pyrophosphate-based sequencing, sample DNA can be sequenced and the extension primer subjected to a polymerase reaction in the presence of a nucleotide triphosphate whereby the nucleotide triphosphate can become incorporated and release pyrophosphate (PPi) if it is complementary to the base in the target position, the nucleotide triphosphate being added either to separate aliquots of sample-primer mixture or successively to the same sample-primer mixture. The release of PPi can be detected to indicate which nucleotide is incorporated. In some embodiments, a region of the sequence product can be determined by annealing a sequencing primer to a region of the template nucleic acid, and contacting the sequencing primer with a DNA polymerase and a known nucleotide triphosphate, (i.e., dATP, dCTP, dGTP, dTTP), or an analog of one of these nucleotides. The sequence can be determined by detecting a sequence reaction byproduct. The sequence primer can be any length or base composition, as long as it is capable of specifically annealing to a region of the amplified nucleic acid template. No particular structure for the sequencing primer is required so long as it can specifically prime a region on the amplified template nucleic acid. The sequencing primer can be complementary to a region of the template that is between the sequence to be characterized and the sequence hybridizable to the anchor primer. The sequencing primer can be extended with the DNA polymerase to form a sequence product. The extension can be performed in the presence of one or more types of nucleotide triphosphates, and if desired, auxiliary binding proteins.

Incorporation of the dNTP can be determined by assaying for the presence of a sequencing byproduct. The nucleotide sequence of the sequencing product can be determined by measuring inorganic pyrophosphate (PPi) liberated from a nucleotide triphosphate (dNTP) as the dNMP is incorporated into an extended sequence primer. This method of sequencing can be performed in solution (liquid phase) or as a solid phase technique.

Sequencing can be performed by SOLiD sequencing. The SOLiD platform can use an adapter-ligated fragment library similar to those of the other next-generation platforms, and can use an emulsion PCR approach with small magnetic beads to amplify the fragments for sequencing. Unlike the other platforms, SOLiD can use DNA ligase and a unique approach to sequence the amplified fragments. Two flow cells can be processed per instrument run, each of which can be divided to comprise different libraries in up to four quadrants. Read lengths for SOLiD can be user defined between 25-50 bp, and each sequencing run can yield up to −100 Gb of DNA sequence data. Once the reads are base called, have quality values, and low-quality sequences have been removed, the reads can be aligned to a reference genome to enable a second tier of quality evaluation called two-base encoding.

Sequencing can be performed by polony sequencing methods. A polony (or PCR colony) can refer to a colony of DNA that is amplified from a single nucleic acid molecule within an acrylamide gel such that diffusion of amplicons is spatially restricted. A library of DNA molecules can be diluted into a mixture that comprises PCR reagents and acrylamide monomer. A thin acrylamide gel (approximately 30 microns (μm)) can be poured on a microscope slide, and amplification can be performed using standard PCR cycling conditions. A library of nucleic acids such that a variable region is flanked by constant regions common to all molecules in the library can be used such that a single set of primers complementary to the constant regions can be used to universally amplify a diverse library. Amplification of a dilute mixture of single template molecules can lead to the formation of distinct, spherical polonies. Thus, all molecules within a given polony can be amplicons of the same single molecule, but molecules in two distinct polonies can be amplicons of different single molecules. Over a million distinguishable polonies, each arising from a distinct single molecule, can be farmed and visualized on a single microscope slide.

An amplification primer can include a 5'-acrydite-modification. This primer can be present when the acrylamide gel is first cast, such that it physically participates in polymerization and is covalently linked to the gel matrix. Consequently, after PCR, the same strand of every double-stranded amplicon can be physically linked to the gel. Exposing the gel to denaturing conditions can permit efficient removal of the unattached strand. Copies of the remaining strand can be physically attached to the gel matrix, such that a variety of biochemical reactions on the full set of amplified polonies in a highly parallel reaction can be performed. A polony can refer to a DNA-coated bead rather than in situ amplified DNA and 26-30 bases can be sequence from $1.6 \times 10^9$ beads simultaneously. It may be possible to scale-up the sequencing to 36 continuous bases (and up to 90 bases) from $2.8 \times 10^9$ beads simultaneously and maybe as many at $10^{10}$.

BEAMing (e.g., Emulsion PCR or ePCR)

High density polony bead arrays can be made using DNA-coated magnetic beads. BEAMing (also referred to herein as ePCR) can refer to a method for clonal implication of individual DNA molecules onto beads. BEAMing can permit amplification of single DNA molecules and simultaneous attachment of the PCR products to beads. BEAMing/ePCR can allow coating of a bead with identical DNA molecules. In some instances, greater than $10^7$ beads can be coated with DNA.

Shotgun Sequencing

In genetics, shotgun sequencing, (e.g., shotgun cloning), can generally be referred to as a method used for sequencing long DNA strands. In shotgun sequencing, multiple overlapping reads for the target DNA can be obtained by performing several rounds of fragmentation and sequencing. Computer programs can use the overlapping ends of different reads to assemble them into a continuous sequence. For example, a single nucleic acid sequence may be sequenced as two separate fragments, wherein each fragment comprises two reads, the respective 3'-5' strand and the 5'-3' strand. None of the four different reads may cover the full length of the original sequence. However, the four reads can be assembled into the original sequence using nucleic acid sequence overlap of their ends, that both to align and order the respective reads.

Another sequencing technology related to shotgun sequencing is pair wise end sequencing. Pair wise end sequencing can perform sequencing from both ends of a read simultaneously, instead of a linear left-right process. Sequencing both ends of the same fragment can be valuable in reconstructing the sequence of the original target fragment. Pair wise sequencing can be performed using fragments of varying sizes, which allows pair-wise end-sequencing of large genomic targets. To apply pair wise sequencing to high-molecular-weight DNA, the DNA can be sheared into random fragments, size-selected (i.e., for example, 2, 10, 50, and/or 150 kb), and cloned into an appropriate vector. The clones can be sequenced from both ends yielding two short sequences. Each sequence can be called an end-read, or read, wherein two reads from the same clone can be referred to as mate pairs. Since the chain termination method can produce reads between 500 and 1000 bases long, in all but the smallest clones, mate pairs may not overlap. The original DNA sequence can be reconstructed from the numerous reads using sequence assembly software. Overlapping reads can be collected into longer composite sequences known as contigs. Contigs can be linked together into scaffolds by following connections between mate pairs. The distance between contigs can be inferred from the mate pair positions if the average fragment length of the library is known and has a narrow window of deviation.

Ion Semiconductor Sequencing

Ion Semiconductor Sequencing is a method of DNA sequencing based on the detection of hydrogen ions that are released during DNA amplification. Ion Semiconductor Sequencing can be referred to as ion torrent sequencing, pH-mediated sequencing, silicon sequencing, and/or semiconductor sequencing. In Ion Semiconductor Sequencing, a complementary strand can be built based on the sequence of a template stand. For example, a microwell containing a template DNA strand to be sequenced can be flooded with a single species of deoxyribonucleotide (dNTP). If the introduced dNTP is complementary to the leading template nucleotide it can be incorporated into the growing complementary strand. This can cause the release of a hydrogen ion that triggers a hypersensitive ion sensor, which indicates that a reaction has occurred. If homopolymer repeats are present in the template sequence multiple dNTP molecules will be incorporated in a single cycle. This can lead to a corresponding number of released hydrogens and a proportionally higher electronic signal.

Solexa Sequencing

Solexa sequencing can be used as a method for generating sequencing data. The method can use adapter-ligated fragments of genomic DNA. The adapter ligated DNA can be randomly attached to a dense lawn of primers that can be attached to a solid surface, typically in a flow cell. The other end of the adapter ligated fragment can hybridize to a complementary primer on the surface. The primers can be extended in the presence of nucleotides and polymerases in a so-called solid-phase bridge amplification to provide double stranded fragments. Denaturation and repetition of the solid-phase bridge amplification can result in dense clusters of amplified fragments distributed over the surface. The sequencing can be initiated by adding four differently labelled reversible terminator nucleotides, primers and polymerase to the flow cell. After the first round of primer extension, the labels can be detected, the identity of the first incorporated bases can be recorded and the blocked 3' terminus and the fluorophore can be removed from the incorporated base. The identity of the second base can be determined in the same way and so sequencing continues. The ligated probes or the amplicons can be bound to the surface via the primer binding sequence, the primer sequence or in some embodiments, the clamp section or a combination thereof. In some embodiments, the probes or the primers used in the amplification may contain specific sections that can be used in the subsequent sequencing step to bind the ligated probes/amplicons to the surface.

Untargeted Sequencing

Untargeted sequencing can be used as a method for generating sequencing data. The methods can provide sequence information regarding one or more polymorphisms, sets of genes, sets of regulatory elements, micro-deletions, homopolymers, simple tandem repeats, regions of high GC content, regions of low GC content, paralogous regions, or a combination thereof. In some cases, the untargeted sequencing can be whole genome sequencing. In some cases, the untargeted sequencing data can be the untargeted portion of the data generated from a target-specific sequencing assay. The methods can generate an output comprising a combined data set comprising target-specific sequencing data and a low coverage untargeted sequencing data as supplement to target-specific sequencing data. Non-limiting examples of the low coverage untargeted sequencing data include low coverage whole genome sequencing data or the untargeted portion of the target-specific sequencing data. This low coverage genome data can be analyzed to assess copy number variation or other types of polymorphism of the sequence in the sample. The low coverage untargeted sequencing (i.e., single run whole genome sequencing data) can be fast and economical, and can deliver genome-wide polymorphism sensitivity in addition to the target-specific sequencing data. In addition, variants detected in the low coverage untargeted sequencing data can be used to identify known haplotype blocks and impute variants over the whole genome with or without targeted data.

Untargeted sequencing (i.e., whole genome sequencing) can determine the complete DNA sequence of the genome at one time. Untargeted sequencing (i.e., whole genome sequencing or the non-exonic portion of whole exome sequencing) can cover sequences of almost about 100 percent, or about 95%, of the sample's genome. In some cases, the untargeted sequencing (i.e., whole genome sequencing or non-exonic portion of the whole exome sequencing) can cover sequences of the whole genome of the nucleic acid sample of about or at least about 99.999%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50%.

Target-Specific Sequencing

Target-specific sequencing can be used as a method for generating sequencing data. Target-specific sequencing is selective sequencing of specific genomic regions, specific genes, or whole exome sequencing. Non-limiting examples of the genomic regions include one or more polymorphisms, sets of genes, sets of regulatory elements, micro-deletions, homopolymers, simple tandem repeats, regions of high GC content, regions of low GC content, paralogous regions, degenerate-mapping regions, or a combination thereof. The sets of genes or regulatory elements can be related to one or more specific genetic disorders of interest. The one or more polymorphisms can comprise one or more single nucleotide variations (SNVs), copy number variations (CNVs), insertions, deletions, structural variant junctions, variable length tandem repeats, or a combination thereof.

In some cases, the target-specific sequencing data can comprise sequencing data of some untargeted regions. One example of the target-specific sequencing is the whole exome sequencing. Whole exome sequencing is target-specific or selective sequencing of coding regions of the DNA genome. The targeted exome is usually the portion of the DNA that translates into proteins, or namely exonic sequence. However, regions of the exome that do not translate into proteins may also be included within the sequence, namely non-exonic sequences. Non-exonic sequences are usually not included in exome studies. In the human genome there can be about 180,000 exons: these can constitute about 1% of the human genome, which can translate to about 30 megabases (Mb) in length. It can be estimated that the protein coding regions of the human genome can constitute about 85% of the disease-causing mutations. The robust approach to sequencing the complete coding region (exome) can be clinically relevant in genetic diagnosis due to the current understanding of functional consequences in sequence variation, by identifying the functional variation that is responsible for both mendelian and common diseases without the high costs associated with a high coverage whole-genome sequencing while maintaining high coverage in sequence depth. Other aspect of the exome sequencing can be found in Ng S B et al., "Targeted capture and massively parallel sequencing of 12 human exomes," Nature 461 (7261): 272-276 and Choi M et al., "Genetic diagnosis by whole exome capture and massively parallel DNA sequencing," Proc Natl Acad Sci USA 106 (45): 19096-19101.

Ontology Data

Data to be used in the methods of the disclosure can comprise ontology data (e.g., gene ontology). Ontology data can correlate between the keywords used for the classification of genotypes. Ontology can refer to a classification system for biological terms and vocabularies. Features classified according to gene ontology can be referred to as "ontology terms". Ontology terms can be constructed in a tree structure together, in which they are related vertically. These terms can be divided into three categories, which can be molecular function, biological process and cellular component. If a gene is multifunctional, multiple gene ontology terms can be allocated to the gene and/or genotype. Gene ontology (GO) can be obtained from the Gene Ontology Consortium. Gene ontology can be applied to describe the roles of genes and gene products in all organisms. Gene Ontology can characterize the relationships between genes and the keywords assigned for each gene. Phenotype ontology can be obtained from the Human Phenotype Ontology. Phenotype Ontology can be applied to describe observed phenotypes in all organisms. Phenotype Ontology can characterize the relationships between phenotypes, diseases, and clinical features.

Gene or phenotype ontologies in an ontology tree can comprise stretching branches of gene or phenotype ontology terms which can be connected with one another by coordinates (nodes) corresponding to ontology terms and the coordinates (nodes) themselves. In some instances, the topmost level of the tree can comprise the whole gene or phenotype ontology and the second highest level can comprise molecular functions, biological process, cellular components, and/or body systems, and levels 3, 4 and 5 are lower levels each forming a tree. As the levels go lower, ontology terms for genes or phenotypes having detailed functions can be provided. In some instances, the ontology tree comprises one of molecular functions, biological processes and cellular components as the topmost level or takes its lower concept as the topmost level.

Ontology data can be obtained from any source that describes a phenotype. Suitable sources can include medical records, doctor's notes, clinical records, disease, traits, phenotypes, pathognomonic features, symptoms, laboratory values, behaviors, conditions, diagnoses, prognoses, genetic history, familial information, and hereditary information.

Genotypes

In some instances, the data of the disclosure can comprise genotype data. Genotype data can be determined from sequencing data. Genotype data can indicate the presence of genetic abnormalities and polymorphisms. Such genotype data can comprise for example, variants, indels, single nucleotide polymorphisms (SNPs), deletions, duplications, insertions, tautomerisms, depurinations, deaminations, replication errors, mutations from non-homologous end joining, mutations from oxidative damage, pyrimidine dimerization, silent mutations, missense mutations, nonsense mutations, transpositions, amplifications, interstitial deletions, loss of heterozygosity mutations, loss of function mutations, gain of function mutations, dominant negative mutations, lethal mutations, reversions, frameshift mutations, neutral mutations, and translocations, or any combination thereof.

Inheritances

The methods of the disclosure can provide for determining the likelihood of inheritance and inheritance patterns of a phenotype. Genetic inheritance can follow a variety of inheritance patterns, which can be traced through lineages and/or be predicted. Inheritance patterns can be classified as Mendelian or non-Mendelian. Mendelian inheritance patterns can refer to the contribution of one allele from each parent for a given trait. Mendelian inheritance patterns can refer to segregation of alleles, single gene inheritance, and dominant-recessive inheritance/phenotypes. Dominant-recessive inheritance patterns can refer to autosomal dominant (i.e., subject has one copy of mutant allele, e.g., Huntington Disease, polycystic kidney disease), autosomal recessive (i.e., subject has two copies of mutant allele, e.g., Cystic fibrosis, Tay-Sachs disease, hemochromatosis), X-linked recessive (i.e., the gene is located on the X chromosome but one normal copy can rescue so that females are typically not affected e.g., Duchenne muscular dystrophy, Hemophilia A), and X-linked dominant (i.e., the gene is located on the X chromosome and one mutant allele is sufficient for phenotype, e.g., incontinentia pigmenti, hypophosphatemic rickets) inheritance patterns. In some instances, an inheritance pattern can be caused by a number of genetic factors, which can be referred to as multifactorial inheritance pattern.

Inheritance patterns can be non-mendelian inheritance patterns. Non-Mendelian inheritance patterns can refer to any inheritance pattern which does not follow Mendelian laws of inheritance (e.g., segregation of alleles). Non-Mendelian inheritance patterns can include extranuclear inheritance (e.g., cytoplasmic inheritance, e.g., maternal inheritance), mitochondrial inheritance, gene conversion, infectious heredity (e.g., viral infection that can transmit a phenotype to progeny), genomic imprinting (e.g., epigenetic marking of an allele), mosaicism (e.g., genetic differences between same cell types within a body, e.g., X-inactivation), and trinucleotide repeat disorders (e.g., expansion of microsatellite tandem repeats), or any combination thereof. Inheritance patterns can also comprise epigenetic inheritance patterns (e.g., methylation state).

Subjects

A subject can be an organism subjected to the methods of the disclosure. In some instances, a subject can be a patient. A patient can be an organism (e.g., a human, dog, cat, companion animal, mouse, rat) that is suffering from a disease and/or in the care of a medical practitioner. A subject can be a mother, father, brother, sister, aunt, uncle, cousin, grandparent, great-grandparent, great-great grandparent, niece, and/or nephew. A subject can be a family member and/or have family members. A subject can be a family member of another subject. A subject can be related by marriage to another subject. A subject can be distantly related to another subject. For example, a subject can be an ancestor, related by $2^{nd}$, $3^{rd}$, $4^{th}$, $5^{th}$, $6^{th}$, $7^{th}$ generation or more removed. A subject can be a living subject related to a non-living subject.

In some instances, a subject of the disclosure can have a disease. In some instances, the subject may show symptoms of a disease but not be diagnosed with a disease. In some instances, the subject may have a disease but not know it. Diseases can include, cancers (e.g., lung, skin, breast, pancreas, liver, colon), cutaneous disease (e.g., acne, glandular rosacea, rhinophyma, otophyma, metophyma, lupus, periorificial dermatitis, dermatitis, psoriasis, Blau syndrome, familial cold urticaria, Majeed syndrome, Muckle-Wells syndrome), endocrine diseases (e.g., adrenal disorders, adrenal hormone excess, diabetes, hypoglycemia, glucagonoma, goiter, hyperthyroidism, hypothyroidism, parathyroid disorders, pituitary gland disorders, sex hormone disorders, hermaphroditism), eye diseases (e.g., disorders of the eyelid, hordeolum, chalazion, disorders of the conjunctiva, conjunctivitis, disorders of the sclera, cornea, iris and ciliary body, scleritis, keratitis, Fuch's dystrophy, disorders of the lens, cataract, disorders of the choroid and retina, chorioretinal inflammation, retinitis, choroidal degeneration, retinal detachments, retinal vascular occlusions, glaucoma, disorders of the vitreous body and globe, disorders of the optic nerve and visual pathways, optic disc drusen, blindness), intestinal diseases, infectious diseases. In some instances, a subject can have a disorder. Disorders can include communication disorders, genetic disorders, neurological disorders, voice disorders, vulvovaginal disorders, mental illness, autism disorders, eating disorders, mood disorders, and personality disorders.

Feature-based Ranking of Genes (FROG)

The disclosure provides methods for analyzing genotype data. FIG. 1 depicts an example method of feature-based ranking of genes. The method for analyzing genotype data can comprise developing a subject-specific ontology profile 105 by collecting attributes attributed to the subject, comparing 110 the ontology profile to public and/or proprietary databases, ranking 115 genes by the similar attributes between the ontology profile and the databases, and annotating 120 variants detected in the sequenced genotype of the subject. A subject-specific ontology profile can comprise words that describe the clinical features (e.g., phenotype) of the subject. A subject-specific ontology profile can be generated from subject-specific ontology data as described above.

A subject-specific ontology profile can be compared to ontology profiles in databases. Databases can comprise gene ontology data for specific genotypes. Public databases can be public or proprietary databases. Examples of databases can include Orphanet, Human Phenotype Ontology (HPO), Online Mendelian Inheritance in Man (OMIM), Model Organism Gene-Knock Out databases, Kegg Disease Database, Reactome, Biocyc, WikiPathways, PID, Gene Ontology, ClinVar, COSMIC, Cancer Gene Census, RegulomeDB, miRbase, GAD, and GWAS Catalog, or any combination thereof.

When a subject-specific ontology profile is compared to ontology profiles in databases, genotypes can be retrieved from the databases that match the ontology profile of the subject. The matched genotype can be used to further populate the subject-specific ontology profile. Some genotypes can have multiple ontology profiles (e.g., phenotypes) associate with them in the database. When a match is found, other ontology profiles of the same genotype can be added to subject-specific ontology profile. This process can be reiterated multiple times to further populate the subject-specific ontology profile.

The genotypes can be ranked by an association score. An association score can indicate how well the retrieved genotypes associate with the subject-specific ontology data. For example, an association score can indicate how well the retrieved genotypes associate with genes, proteins, RNAs, pathognomonic features, clinical features, diseases, traits, symptoms, laboratory values, diagnoses, behaviors, conditions, differential diagnoses, prognoses, genetic history, familial information, hereditary information, human phenotypes, non-human phenotypes, genotypes, genomes, exomes, pathways, disease ontology, phenotype ontology, and gene ontology, or any combination thereof.

An association score can be a positive, neutral, or negative score. A positive association score can indicate a large amount of correlation between the genotypes of the database and the ontology data of the subject. A neutral association score can indicate a neutral amount of correlation between the genotypes of the database and the ontology data of the subject. A negative association score can indicate a low amount of correlation between the genotypes of the database and the ontology data of the subject.

An association score can be a weighted score. The weighting can take into account the number of clinical features present in the subject and the genotype, the number of diagnoses present in the subject and the genotype, and the number of affected individuals in a family that have the clinical feature and/or diagnosis. A genotype can be correlated to one or more ontology categories. An association score for each genotype can be equal to the sum of the weighted association scores for each clinical feature and/or diagnosis that the genotype is associated with. For example, a genotype can be weakly associated with a first clinical feature (e.g., ontology category), and strongly associated with a second clinical feature (e.g., ontology category). The association score of the genotype can comprise the sum of the weak association score and the strong association score. In some instances, the association score can be an average, a median, a mode, or any other statistical measurement of a plurality of association scores.

The weighting of genotype scores can be related to the strength of association between a genotype and an ontology category. Genotypes that are strongly related to a clinical feature and/or diagnosis (e.g., ontology category) can be weighted more than genotypes that are weakly related to a clinical feature and/or diagnosis. For example, genotypes that are correlated to pathognomonic features can be weighted more than if the genotype was correlated to a less specific clinical feature.

In some instances, the association score can be a lower score than expected because the retrieved genotypes associated with the subject-specific ontology data can retrieve a new ontology feature not accounted for in the subject-specific ontology profile. For example, a subject-specific ontology profile comprising ontology for obesity but not cancer may retrieve a number of genes related to obesity, wherein a subset of those genes may also have ontology for cancer. In some instances, the new ontology feature retrieved by the genotype in the database may be added to the subject-specific ontology profile and the process may be iteratively repeated. In some instances, the new feature retrieved by the genotype in the database may be used as a diagnosis and/or to inform a medical treatment plant.

Genotypes can be ranked according to their association score. Rankings can be indicative of likelihood of a gene to be causative of a feature (e.g., clinical feature, diagnosis, and/or Mendelian-inherited disease and/or trait). Ranked genotypes can be compared to the sequencing data of the subject and/or family of the subject. The sequencing data of the subject and/or family of the subject can generate information about the genotype variants of the subject. The ranked genotypes (e.g., genotypes from databases), can be compared to the genotypes of the subjects to determine if variants of the subject can be causative of a clinical feature of the subject. For example, an association score can rank gene 1 as highly likely to be causative for disease 1 of the subject and sequenced gene 1 from the subject shows a single nucleotide polymorphism; therefore, the single nucleotide polymorphism may be considered causative of disease 1. In this way, comparing the ranked genotypes to the subject-sequenced genotypes can facilitate causative variant discovery.

Variant Inheritance Pattern Ranking (VIPR)

Figure 2:
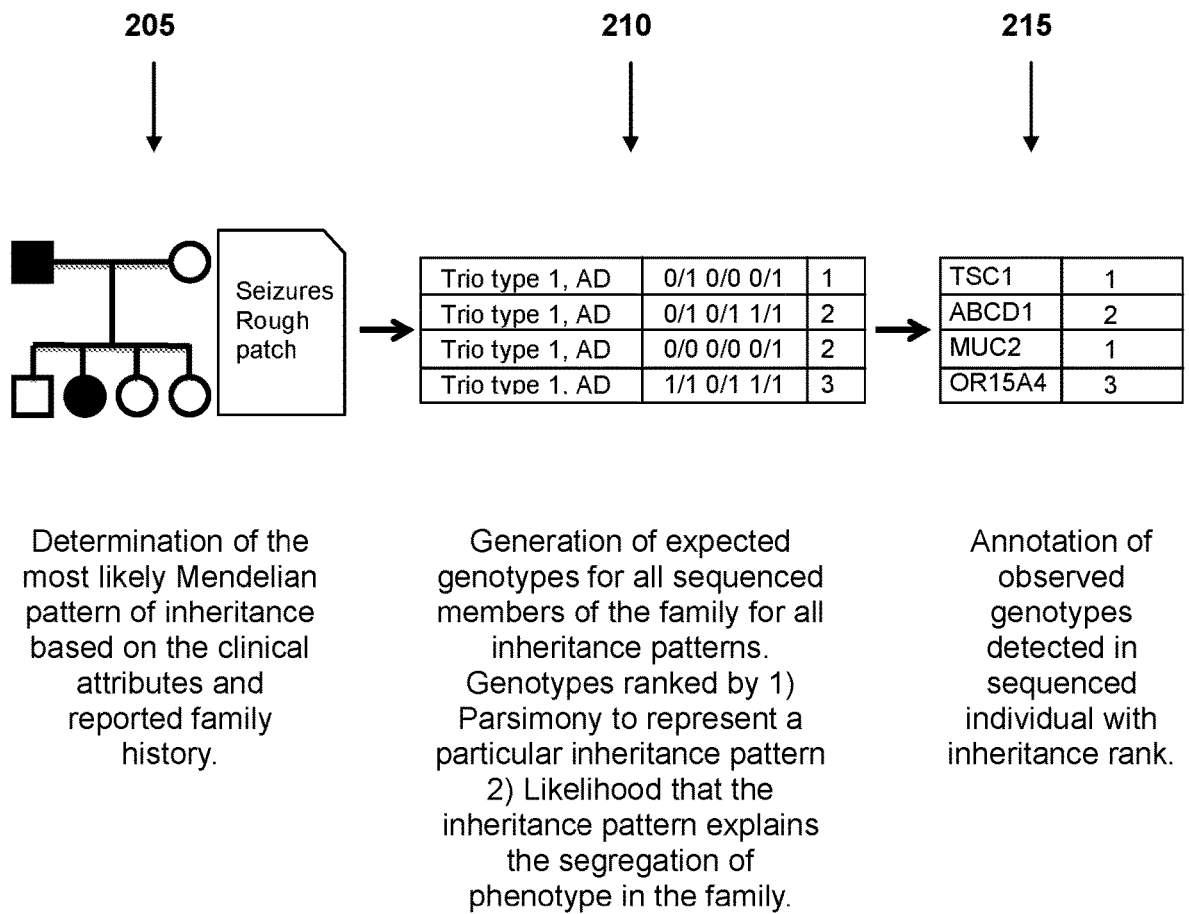
FIG. 2 illustrates an example of the variant inheritance pattern ranking (VIPR) method of genotype analysis.

The disclosure provides methods for analysis of genotype data comprising determining inheritance patterns of genotypes. FIG. 2 depicts an example method of variant inheritance pattern ranking. For example, variant inheritance pattern ranking can comprise determination 205 of most likely inheritance patterns based on an ontology profile of the family, generation 210 of expected genotypes for all inheritance patterns, ranking 215 of expected genotypes against the likelihood of following a particular inheritance pattern, and annotation of genotypes observed in the sequenced subject. In some instances, the methods provide for generating expected genotypes of a subject and members of a subject's family. Expected genotypes can be generated based on inheritance patterns. Expected genotypes can be created for every possible inheritance pattern.

The expected genotypes can be ranked according to an inheritance pattern score that represents the likelihood of each inheritance pattern to explain the pattern of disease observed in the family and the ontology profile of the family. For example, vertical transmission of disease from generation to generation is most likely to be explained by genotypes consistent with a dominant mode of inheritance. The expected genotypes can be ranked according to the overall likelihood of the expected genotype to explain an inheritance pattern. The ranking can take into account genetic events like penetrance, new mutations, and recurrent mutations that may be needed to match an expected inheritance pattern. An inheritance pattern score can also take into account segregation of a phenotype in the subject and/or subject's family. Segregation can refer to separation of two alleles of a gene to each of the progeny. In some instances, a segregation pattern can refer to the pattern of the segregation of a genotype. A segregation pattern can take into account genetic linkage and pseudolinkage. Exemplary segregation patterns can include, for example, alternate segregation patterns, alternate-1 segregation patterns, alternate-2 segregation patterns. Ranking can be based on a statistical calculation of fit. Ranking can be based on rank categories determined by clinical judgment.

Observed genotypes from sequencing data generated from sequencing a subject and/or a subject's family members can be ranked according to the corresponding expected genotype. This type of ranking of observed genotypes in comparison to expected genotypes can facilitate causative variant disclosure and indicate which observed genotypes are more likely to be inherited.

Combined Methods

In some instances, the analysis of genotype data can proceed first by ranking according to an association score (FROG) and then ranking according to an inheritance pattern score (VIPR). In some instances, the analysis of genotype data can proceed first by ranking according to an inheritance pattern score (VIPR) and then an association score (FROG).

Figure 3:
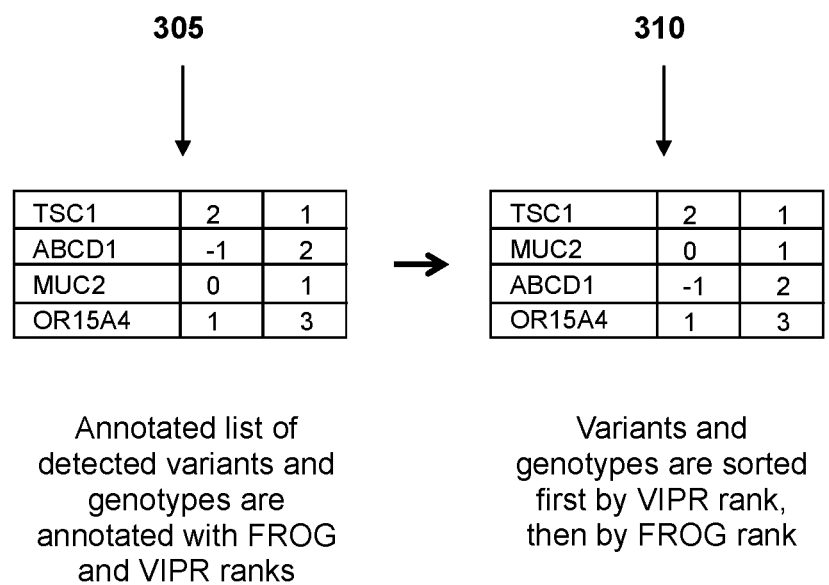
FIG. 3 illustrates an example of the combined FROG and VIPR methods of genotype analysis.

FIG. 3 depicts an example combined method of the disclosure. For example, an annotated list of the genotypes of the subject (e.g., sequencing data) can be ranked 305 according to an association score and an inheritance pattern score. The genotypes in the list can be sorted 310 according to an inheritance pattern score and then by an association score.

Control Systems

Figure 4:
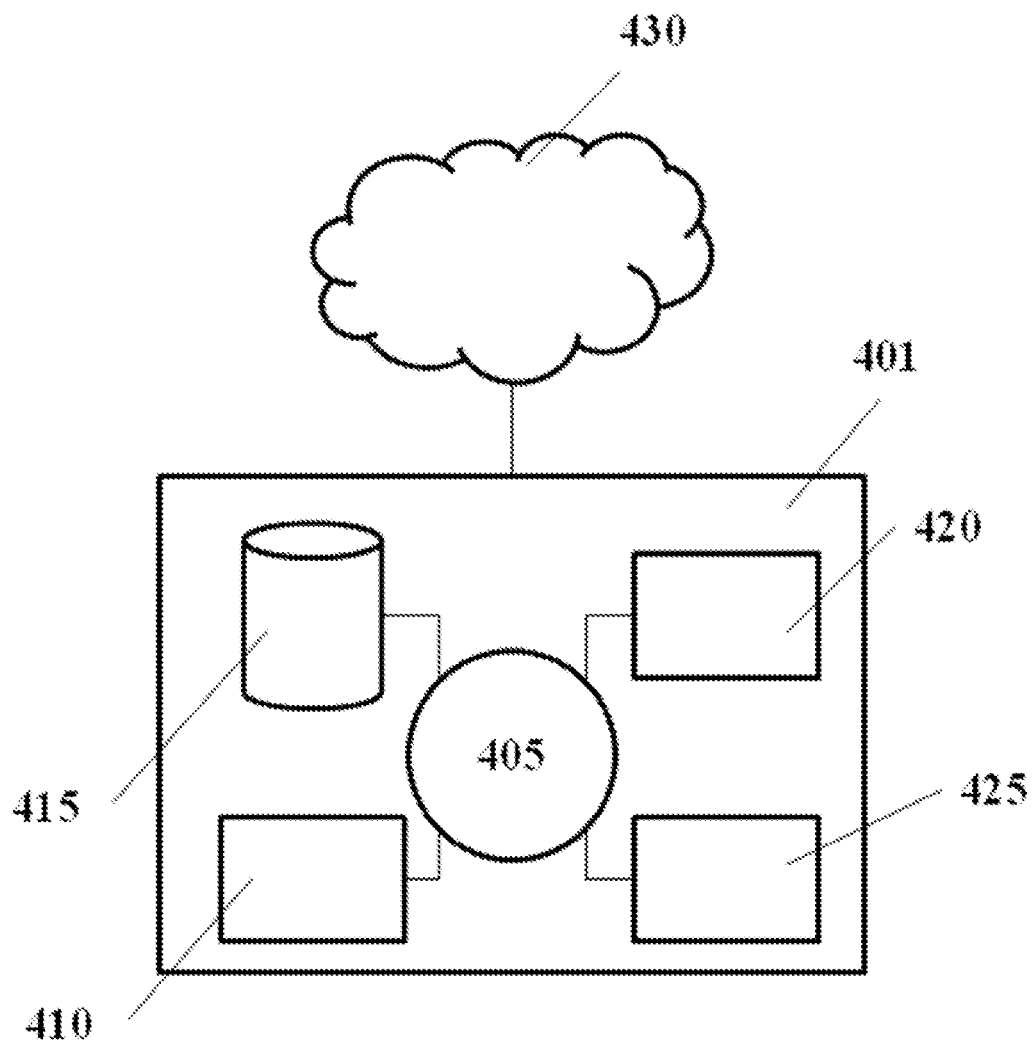
FIG. 4 schematically illustrates an example control system implementing methods of the present disclosure.

The present disclosure provides computer control systems that are programmed to implement methods of the disclosure. FIG. 4 shows a computer system 401 that is programmed or otherwise configured to analyze genotype data according to methods of the disclosure. The computer system 401 can regulate various aspects of genotype analysis of the present disclosure, such as, for example, analysis by inheritance pattern scores, and/or analysis by association pattern scores.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. Examples of operations performed by the CPU 405 can include fetch, decode, execute, and writeback. The CPU 405 can be processor that is programmed for performing the methods of feature-based ranking of genes (FROG), variant inheritance pattern ranking (VIPR), determining segregation patterns, determining inheritance patterns, determining association scores, and ranking phenotypes, genotypes and any data associated with the methods of the disclosure.

The storage unit 415 can store files, such as drivers, libraries and saved programs. The storage unit 415 can store programs generated by users and recorded sessions, as well as output(s) associated with the programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display that comprises a user interface (UI) for providing, for example, a display, graph, chart and/or list in graphical and/or numerical form of the genotype analysis according to the methods of the disclosure, which may include inheritance analysis, causative variant discovery analysis, and diagnosis. Examples of UI's include, without limitation, a graphical user interface (GUI) and web-based user interface.

The data generated by the ranking can be displayed (e.g., on a computer). The data can be displayed in a numerical and/or graphical form. For example, data can be displayed as a list, as statistics (e.g., p-values, standard deviations), as a chart (e.g., pie chart), as a graph (e.g., line graph, bar graph), as a histogram, as a map, as a heat map, as a timeline, as a tree chart, as a flowchart, as a cartogram, as a bubble chart, a polar area diagram, as a diagram, as a stream graph, as a Gantt chart, as a Nolan chart, as a smith chart, as a chevron plot, as a plot, as a box plot, as a dot plot, as a probability plot, as a scatter plot, and as a biplot, or any combination thereof.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which may depend upon a variety of conditions and variables. Various modifications in form and detail of the embodiments of the invention will be apparent to a person skilled in the art. It is therefore contemplated that the invention shall also cover any such modifications, variations and equivalents.

EXAMPLES

Example 1: Feature-Based Ranking of Genes (FROG)

Methods and systems of the present disclosure provide for ranking genes based on features developed in a subject-specific ontology profile. In some instances, a subject has a phenotype (e.g., a disease, trait, characteristic). The phenotype has several attributes (e.g., features, ontology features, clinical terms) associated with the phenotype. A subject-specific ontology profile is developed in which the ontology profile comprises a list of attributes (e.g., clinical terms) associated with the phenotype. The attributes are obtained from clinical terms observed in the sequenced subject and/or the family members of the subject such as clinical features, diagnoses, laboratory values, pertinent negatives, and pertinent positives. The attributes comprise clinical terms that represent that same underlying feature (e.g., failure to thrive, poor weight gain). Clinical terms are excluded that are likely unrelated to clinical presentation of query (e.g., heart attacks in older family members). Clinical terms are also obtained from the generation of alternate clinical feature search terms that represent synonyms of the observed attributes (e.g., "hypertelorism" and "widely spaced eyes")

A rank is applied to each feature based on its specificity, the number of times it was observed in the family, and/or its being the "cardinal feature" of the presenting clinical picture. Candidate loci (e.g., genes, genomic regions) that have been previously described to be associated with clinical features are searched. The search is conducted one clinical term at a time using public and proprietary databases linking clinical terms to candidate loci. Databases that are searched include, without limitation: HGMD, OMIM, HPO, the Personalis Disease Variant Database, primary literature, ClinVar, DGV, dbSNP, Genetic Test Registry, GWASCatalog, GAD, COSMIC, Cancer Gene Census.

Candidate loci (e.g., genes, genomic features) that are related to candidate loci that have been previously described to be associated with clinical features (e.g., ontology) are searched. These candidate loci include for example, binding partners and/or genes involved in the same pathway. The search is conducted one clinical term at a time using public and proprietary databases linking clinical terms to candidate loci.

For all identified candidate loci, a reciprocal overlap is calculated based on the attributes observed in the subject and the clinical features that have been described for that gene. Genes with many attributes annotated to them receive higher ranks depending on their assigned rank, and on the reciprocity of the overlap, taking into consideration pathognomonic features, and/or specificity of features for genes. Genes not directly linked to attributes that are deemed candidates by virtue of their interaction with, or included in the pathway of, genes known to be directly linked to attributes are assigned fraction ranks that are additive over the number of clinical terms that they can be secondarily linked to. Genes with attributes annotated to them that do not match any of the observed attributes are assigned a final negative rank. Final ranks are annotated onto the variant genotype files generated during sequencing.

The ranking indicates how likely a candidate loci and/or observed genotype is to contribute to an observed phenotype. The ranking also indicates new variants that can be causative of the phenotype of the subject.

Example 2: Variant Inheritance Pattern Ranker
(VIPR)

Methods and systems of the present disclosure provide for ranking genotypes based on inheritance patterns. In some instances, a subject has a phenotype (e.g., disease, polymorphism, etc). A subject's genomic material is sequenced. Clinical information about the subject and the family members of the subject are obtained (e.g., phenotypes, attributes). The clinical information, the sequenced samples, and clinical judgment is used to determine the most likely mode(s) of inheritance (e.g., inheritance pattern) for a subject and members of the family of the subject. A pedigree structure and the most likely mode(s) of inheritance are specified to a tool that queries a computer file to retrieve the most likely genotypes to be explanatory of the phenotypes. The file ranks genotypes based on a tiering system constructed from clinical judgment regarding the most likely genotypes to be observed under each family structure. The file ranks genotypes based on a statistical calculation of the most likely inheritance pattern given the family structure, the pattern of phenotypes in the family, and modeling for various penetrance values. The final VIPR rank for each genotype is annotated onto the variant genotype files generated during sequencing. The ranking of observed genotypes determines which observed genotypes are most likely to be inherited to contribute to an observed phenotype of the subject and/or family members of the subject.

Example 3: Feature-Based Ranking of Genes and Variant Inheritance Pattern Ranker The FROG and VIPR ranks obtained as described in Examples 1 and 2 are used to prioritize manual review of genotype variants according to the American College of Medical Genetics (ACMG) Guidelines for variant interpretation. The variants are sorted first by their FROG rank and then by their VIPR rank. In some instances, the variants are sorted first by their VIPR rank and then by their FROG rank.

Methods and systems of the present disclosure can be combined with and/or modified by other methods and systems, such as those described in, for example, U.S. Pat. No. 6,754,655, U.S. Patent Pub. No. 2014/0200147, U.S. Patent Pub. No. 2009/0183268, U.S. Patent Pub. No. 2013/0073217 and PCT/US14/53295, each of which is entirely incorporated herein by reference.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A computer-implemented method, comprising:
   a. receiving data relating to one or more phenotypes of a subject or family members of the subject;
   b. receiving data relating to one or more genotypes of the subject or family members of the subject;
   c. using a programmed computer processor, ranking a plurality of genes based at least in part on their association score with the one or more phenotypes, wherein the association score is a weighted score, wherein the weighted score is based on (i) familial and/or hereditary information; (ii) specificity of a clinical feature-to-gene relationship; and/or (iii) reciprocity of clinical features and/or diseases associated with the genes;
   d. using the programmed computer processor, ranking the plurality of genes of the one or more genotypes using an inheritance pattern score that is based on allowed genotypes, and wherein the inheritance pattern score is at least partially based on a likelihood of the genotype to explain a particular inheritance pattern, a segregation pattern, or a combination thereof; and
   e. generating an output with at least a subset of the plurality of genes ranked based on the association score and inheritance pattern score.

2. The method of claim 1, wherein the one or more phenotypes comprise one or more diseases, traits, symptoms, laboratory values, diagnoses, behaviors, conditions, or a combination thereof.

3. The method of claim 1, wherein the association score comprises the association of one or more genes with one or more of: genes, proteins, RNAs, pathognomonic features, clinical features, diseases, traits, symptoms, laboratory values, diagnoses, behaviors, conditions, differential diagnoses, prognoses, genetic history, familial information, hereditary information, human phenotypes, non-human phenotypes, genotypes, genomes, exomes, pathways, disease ontology, phenotype ontology, and gene ontology, or any combination thereof.

4. The method of claim 3, wherein the association score represents a positive association.

5. The method of claim 3, wherein the association score represents a neutral association.

6. The method of claim 3, wherein the association score represents a negative association.

7. The method of claim 3, wherein the association score is comprised of the combination of ranks of two or more genes.

8. The method of claim 3, wherein the plurality of genes are ranked in computer memory.

9. The method of claim 4, wherein the plurality of genes is ranked substantially or entirely based on the association score.

10. The method of claim 1, wherein the association score is related to the number of clinical features and/or diagnoses associated with the plurality of genes.

11. The method of claim 1, wherein the familial and/or hereditary information comprises the number of affected individuals in a family that is exhibiting a clinical feature and/or diagnosis.

12. The method of claim 1, wherein the specificity of the clinical feature-to-gene relationship comprises pathognomonic features.

13. The method of claim 1, wherein the output comprises a comparison of the data based on the association score that identifies the likelihood of one or more of: causative genes, neutral genes and non-causative genes.

14. The method of claim 1, wherein the data comprises two or more genotypes.

15. The method of claim 14, wherein the ranking comprises ranking the two or more genotypes.

16. The method of claim 15, wherein the two or more genotypes are ranked based on the inheritance pattern score.

* * * * *